United States Patent
Chang et al.

(10) Patent No.: US 6,620,804 B2
(45) Date of Patent: Sep. 16, 2003

(54) SELENOPHENE ANTI-TUMOR AGENTS

(75) Inventors: Ching-jer Chang, West Lafayette, IN (US); Curtis L. Ashendel, West Lafayette, IN (US); Darrick Kim, Chicago, IL (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 10/061,480

(22) Filed: Feb. 1, 2002

(65) Prior Publication Data

US 2003/0028015 A1 Feb. 6, 2003

Related U.S. Application Data

(63) Continuation of application No. 09/180,514, filed as application No. PCT/US97/09717 on Jun. 3, 1997, now abandoned.
(60) Provisional application No. 60/019,095, filed on Jun. 3, 1996.

(51) Int. Cl.[7] .................... C07D 421/14; C07D 421/04; A61K 31/381; A61K 31/341; A61P 35/00
(52) U.S. Cl. .................. 514/183; 514/461; 514/444; 540/1; 548/517; 548/518; 548/527; 549/59; 549/472; 549/473; 549/60
(58) Field of Search ................ 514/183, 461, 514/444; 540/1; 548/517, 518, 527; 549/59, 472, 60, 473

(56) References Cited

U.S. PATENT DOCUMENTS 5,578,636 A  11/1996  Chang et al. ............... 514/444

OTHER PUBLICATIONS

Chem. Abstr., vol. 113, No. 21, Nov. 19, 1990 (Columbus, OH, USA), p. 695, col. 2, the abstract No. 191079S, Shabana et al., "Synthesis of Mixed Oligomeric Heteroarylenes Containing Unsubstituted Furan, Thiopene, and Selenophene Rings; Their UV Spectra and Oxidation Potentials." Phosphorus, Sulfur, Silicon Related Elem. 1990, 48(1–4), 239–44 (Eng.), see entire Abstract.
Chem. Abstr., vol. 112, No. 5, Jan. 29, 1990 (Columbus, OH, USA), p. 554, col. 12, the abstract No. 35596g, Zimmer, H. et al., "Synthesis of Mixed Oligomeric Heteroarylenes Containing Furan, Thiopene, and Selenophene Rings; Their UV Spectra and Oxidation Potentials." Phosphorus, Sulfur, Silicon Related Elem. 1989, 42(3–4), 171–6 (Eng.), see entire Abstract.
Chem. Abstr., vol. 110, No. 15, Apr. 10, 1989 (Columbus, OH, USA), p. 650, cols. 1–2, the abstract No. 134566n, Shabana, R. et al. "Synthesis of Mixed Heteroarylenes Containing Thiopene and Selenophene Rings. Their UV Spectra and Oxidation Potentials." J. Chem. Soc. Chem. Commun. 1988, (15), 988–9 (Eng.), see entire Abstract.
Photochemistry and Photobiology, vol. 39, No. 4, pp. 521–524, 1984 (Great Britian), "Research Note: Comparison Of The Phototoxicity Of α–Terthienyl With That Of A Selenium and Of An Oxygen Analogue."
Mikhaleva, et al., Synthesis of 2–(2–Selenienyl)Pyrrole from Methyl–2–Selenienylketoxime and Acetylene, Chem. Heterocycl. Comp., vol. 28, No. 5, pp. 599–601 (1992).
Fringuell, et al., Heteroaromatic Rings as Substituents, J. Chem Soc. Perkin Tansactions, vol. 2, pp. 971–975 (1980).
Novak, et al., Electronic Structure of Bichalcophenes, J. Phys. Chem., vol. 98, No. 20, pp. 5240–5243 (1994).
Yui, et al., Extensively Conjugated Homologues of Selenophene—TCNQ as New Electron Acceptors, Chem. Letters, pp. 1179–1182 (1988).

*Primary Examiner*—Mark L. Berch
*Assistant Examiner*—Kahsay Habte
(74) *Attorney, Agent, or Firm*—Barnes & Thornburg

(57) ABSTRACT

Novel selenophene compounds useful as anti-tumor agents are described. Preferred compounds include compounds of formula I:

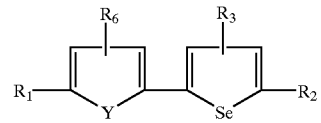

wherein $R_1$ and $R_2$ are independently selected from the group consisting of;

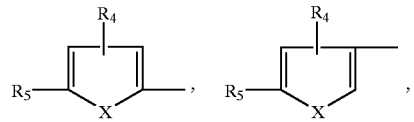

H, CHO, $CH_2OH$ and $CH_2NH_2$; and

X and Y are independently selected from the group consisting of Se, S, O, $NCH_3$ and NH. Pharmaceutical compositions and a method for treating patients having tumors utilizing the disclosed selenophene compounds are also described.

23 Claims, No Drawings

SELENOPHENE ANTI-TUMOR AGENTS

CROSS REFERENCE TO RELATED APPLICATIONS

This application is a continuation application of U.S. patent application Ser. No. 09/180,514, filed on Nov. 11, 1998, now abandoned which is a U.S. national application of international application Ser. No. PCT/US97/09717, filed Jun. 3, 1997, which claims priority to U.S. provisional application Ser. No. 60/019,095, filed Jun. 3, 1996.

GOVERNMENT RIGHTS

This invention was made with United States Government support under Grant No. UO1 CA50743, awarded by the National Cancer Institute. The United States Government has certain rights in the invention.

FIELD OF THE INVENTION

The present invention relates to compositions and a method for treating a patient having a tumor. More specifically, the present invention relates to the treatment of such patients with an effective amount of a selenophene derivative.

BACKGROUND AND SUMMARY OF THE INVENTION

The control and cure of cancer represents one of our most challenging health problems. The treatment of cancer can be approached by several modes of therapy including surgery, radiation, chemotherapy or a combination of any of these treatments. Chemotherapy continues to be an indispensable therapy for inoperable or metastatic forms of the disease.

The selection of natural compounds, or the synthesis of new compounds having effective anticancer activity is complicated by the still limited knowledge of cancer cell biology and biochemistry. Therefore, development of new effective anti-tumor agents will remain heavily dependent on screening compounds to discover novel compounds having cytotoxic activity. Preferably, such compounds exhibit enhanced cytotoxicity against tumor cells relative to their cytotoxicity to normal cells.

The success of novel antitumor drug development programs is dependent on the initial identification of antitumor agents. Thus the discovery of antitumor agents requires the systematic screening of a large number of natural products and synthetic compounds.

The mouse L1210 leukemia cell line was initially the preferred model system used for screening natural compounds for antitumor activity. However, the P388 murine leukemia system was found to be more sensitive and predictive than L1210 leukemia system, and has been used as primary screen during the past decade. Systematic screening for compounds exhibiting toxicity to these two leukemia cell lines has resulted in the isolation of a large number of active natural products. However, the anticancer activities of these compounds were predominantly in leukemia, lymphoma and a few rare tumors. Low clinical efficacy, or the lack of clinical efficacy of known chemotherapeutics against slower growing solid tumors, is a serious concern.

It has been recognized that the use of a single antileukemia screening system could bias the end results and lead to the isolation of compounds only active in the treatment of fast growing tumors. In addition, the use of a single anti-leukemia screening system may not detect novel compounds with high specificities for particular cell lines. It is also likely that many novel compounds with possible anti-tumor activity have remained undetected by the less sensitive in vivo models due to the low concentrations at which many active natural products occur Considering the diversity of tumors in terms of cell type, morphology, growth rate and other cellular characteristics, the U.S. National Cancer Institute (NCI) has developed a "disease-oriented" approach to antitumor activity screening (M. R. Boyd, in "Principle of Practice of Oncology" J. T. Devita, S. Hellman, S. A. Rosenberg (Eds.) Vol. 3, PPO Update, No. 10, 1989). This in vitro prescreening system is based on the measurement of antitumor cytotoxicity against human tumor cell line panels consisting of approximately 60 cell lines of major human tumors (including leukemia and slower growing tumor cells such as lung, colon, breast, skin, kidney, etc.). The most important advantage of the new in vitro screening panels is the opportunity to identify compounds that are selectively more cytotoxic to cells of slowly growing solid tumors than to rapidly growing leukemia cells.

The cytotoxicity profile of the NCI human tumor cell panels displays the tumor specificity of a given compound, however the assay does not assess the toxicity of that compound to normal human cells. Accordingly a second bioassay is utilized to measure the selective cytotoxicity against certain types of tumor cells verses normal human cells.

The growth and differentiation of cells are regulated by signaling cascades induced by various mitogenic proteins (J. Kuijan and B. L. Taylor, "Signal Transduction," Academic Press, New York, N.Y. 1994) that often are encoded by proto-oncogenes. The overexpression, amplification or mutation of the oncoprotein is critically involved in the initiation, progression and metastasis of malignant cells (R. A. Weinberg, "Oncogenes and the Molecular Origins of Cancer," Cold Spring Harbor Laboratory Press, Cold Spring Harbor, N.Y., 1989). Many oncoproteins alter normal cellular growth regulation by modulating the intracellular signaling pathways from the membrane to the nucleus. Therefore, cancer may be considered as a disease of cellular signal transduction, which presents a novel approach for anticancer therapy. One of the critical enzymes involved in the oncoprotein signal transduction is protein kinase C (U. Nishizuka, *Nature,* 308, 693, 1984 and *Science,* 233, 305, 1986). Thus, the determination of a compound's ability to inhibit protein kinase C activity has become a good prognostic for discovering novel anticancer agents (A. Basu, *Pharmac Ther,* 59, 257, 1993). Furthermore it is anticipated that the selenophene compounds will demonstrate selectivity for certain class members of protein kinases, including protein kinage C. Inhibition of a specific classes of protein kinases will allow the treatment of other diseases associated with defects in signaling transduction.

Selenophenes are selenium containing heterocyclic compounds that are analogs of naturally occurring thiophene, furan and pyrrole compounds. Selenophenes have been found to be effective antitumor agents, and exhibit enhanced cytotoxicity against slow growing tumor cells, selective cytotoxicity against human renal, ovarian tumor cells, and skin tumor cells; and exhibit inhibition of protein kinase C.

In accordance with this invention there is provided a method for the treatment of cancer which utilizes selenophene compounds of the formula I:

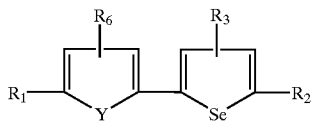

wherein $R_1$ and $R_2$ are independently selected from the group consisting of;

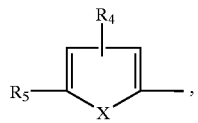

H, CHO, $CH_2OH$ and $CH_2NH_2$;

X and Y are independently selected from the group consisting of Se, S, O, $NCH_3$ and NH;

$R_3$, $R_4$, $R_5$ and $R_6$ are independently selected from the group consisting of H, CHO, $CH_2OH$ and $CH_2NH_2$; cyclodextrin complexes of such compounds; and when $R_3$, $R_4$, $R_5$ or $R_6$ is $CH_2NH_2$, the pharmaceutically acceptable salt of the compound represented thereby.

Further in accordance with this invention there are provided novel cytotoxic compounds of the above formula and chemotherapeutic pharmaceutical compositions containing said compounds in anti-tumor effective amounts.

Additional objects, features, and advantages of the invention will become apparent to those skilled in the art upon consideration of the following detailed description of preferred embodiments exemplifying the best mode of the invention as presently perceived.

DETAILED DESCRIPTION OF THE INVENTION

The present invention is directed to selenophene compounds, their pharmaceutical compositions and methods utilizing such compounds/compositions for treating patients having tumor. The selenophene compounds are effective antitumor agents against slow growing tumors, and generally have been found to exhibit high selective cytotoxicity for individual tumor cell lines.

The present selenophene compounds are readily prepared using art-recognized chemical synthesis procedures as exemplified in Example 1 and Examples 3–8. This invention is further envisioned from the chemical concept on the basis of a coherent design as shown in scheme 3 in Example 2. This chemical concept provides the foundation for conceiving the preparation and utility of numerous "hybrid" selenophene compounds containing other related five-membered heterocycles, such as furan, thiophene and pyrrole, and their analogs. Moreover, the practice of this chemical concept is substantiated by Example 2 and Examples 9–33. The anticancer utility of these hybrid selenophene compounds is manifested by (a) selective cytotoxicity for human renal carcinoma cells in comparison to normal human renal cells (Table 1), (b) antitumor cytotoxicity against a variety of human tumor cells (Example 53), (c) in vivo antitumor activity against human lung tumor (Example 54) and (d) inhibition of protein kinase C activity (Table 2).

In corroboration with the above chemical concept, a versatile, alternative synthetic design is further conceived for the preparation of relevant "hybrid" selenophene compounds as in the scheme shown in Example 34. The practice of this synthetic design is supported by Examples 34–50. The anticancer utility of these hybrid selenophene compounds is indicated by (a) selective cytotoxicity for human renal carcinoma cells in comparison to normal human renal cells (Table 1), (b) antitumor cytotoxicity against a variety of human tumor cells (Example 53), (c) in vivo antitumor activity against human lung tumor (Example 54) and (d) inhibition of protein kinase C (Table 2).

The compounds of the present invention are selenophene compounds of the formula I:

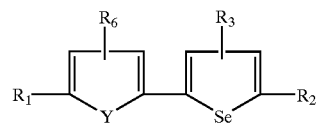

wherein $R_1$ and $R_2$ are independently selected from the group consisting of;

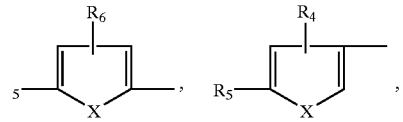

H, CHO, $CH_2OH$ and $CH_2NH_2$;

X and Y are independently selected from the group consisting of Se, S, O and NR;

R is H or $C_1$–$C_7$ alkyl;

$R_3$, $R_4$, $R_5$, and $R_6$ are independently selected from the group consisting of nitro, amino, alkoxy, cyano, chloro, bromo, iodo, $C_1$–$C_7$ alkyl or haloalkyl, $C_1$–$C_7$ alkenyl or haloalkenyl, $C_1$–$C_4$ alkanoyloxy methyl, $CH_2OR_7$, $COR_8$, $CH_2NR_9R_{10}$, $CH(OR_7)R_{11}$, $CH=CR_{12}R_{13}$, $CH=NR_{14}$, $CH_2SC(NH)NH_2$ and $C\equiv CR_{15}$ wherein $R_7$ is H, $CO(CH_2)_2CO_2H$, $(CH_2)_2OCH_3$, $C_1$–$C_4$ alkyl or $COC_1$–$C_{17}$ alkyl;

$R_8$ is H or $C_1$–$C_7$ alkyl;

$R_9$ and $R_{10}$ are independently H, CN, $C_1$–$C_4$ alkyl, or mono- or di-hydroxy$C_2$–$C_4$ alkyl;

$R_{11}$ is $C_1$–$C_7$ alkyl, or $C_1$–$C_7$ alkenyl;

$R_{12}$ and $R_{13}$ are independently H, $C_1$–$C_7$ alkyl, $COOR_8$, CN, $CH(OR_7)COOR_8$, Br, CO-thienyl, $COC_6H_4OH$ (p);

$R_{14}$ is $NHR_7$ or $OR_8$;

$R_{15}$ is $COOR_8$, $CH(OR_7)CH_2OR_{16}$ or $CH(OCOC_1$–$C_4$ alkyl)$CH_2OR_8$;

$R_{16}$ is H, $COCH_2CH_2CO_2H$, or $COC_1$–$C_7$ alkyl; cyclodextrin complexes of such compound and when $R_3$, $R_4$, $R_5$ or $R_6$ is $CH_2NR_6R_7$, the pharmaceutically acceptable salt of the compound represented thereby.

In one preferred embodiment of this invention there is provided anti-tumor selenophenes of the above formula I, wherein $R_2$ is

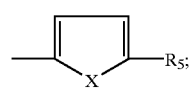

X and Y are independently selected from the group consisting of S, Se and NH;

$R_1$, $R_3$, and $R_6$ are H; and $R_5$ is selected from the group consisting of CHO or $CH_2OH$; and cyclodextrin complexes of such compounds. These compounds have been demonstrated to exhibit cytotoxic selectivity against transformed human cells (See Table 1).

In another preferred embodiment of this invention there is provided anti-tumor selenophenes of the above formula I wherein $R_1$ is

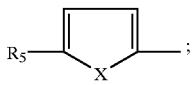

X and Y are independently selected from the group consisting of S, Se and NH;

$R_2$, $R_3$, and $R_6$ are H;

$R_5$ is selected from the group consisting of CHO or $CH_2OH$; and cyclodextrin complexes of such compounds.

Other preferred compounds in accordance with this invention are selenophenes of formula I:

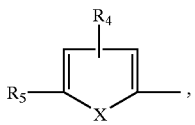

wherein $R_1$ and $R_2$ are independently selected from the group consisting of;

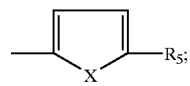

H, CHO, $CH_2OH$ and $CH_2NH_2$;

X and Y are independently selected from the group consisting of Se, S, O, $NCH_3$, and NH;

$R_3$, $R_4$, $R_5$ and $R_6$ are independently selected from the group consisting of H, CHO, $CH_2OH$ and $CH_2NH_2$; cyclodextrin complexes of such compounds; and when $R_2$ or $R_3$ is $CH_2NH_2$, the pharmaceutically acceptable salt of the compound represented thereby; with the proviso, that when $R_2$ is

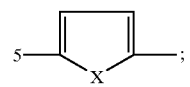

$R_1$ is other than

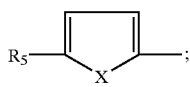

and when $R_1$ is $R_2$ is other than

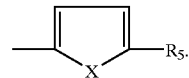

In accordance with another embodiment of the present invention novel intermediates of Formula II are also provided:

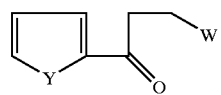

wherein W is selected from the group consisting of $N(CH_3)_2$ and

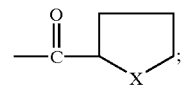

and X and Y are independently selected from the group consisting of Se, S, O, $NCH_3$ and NH.

One aspect of the present invention is a method of preparing the compounds of Formula I through an intermediate a compound of the formula

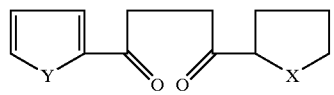

in accordance with the general methods of schemes 1–4 as described hereinbelow, wherein X and Y are independently selected from the group consisting of Se, S, O, $NCH_3$ and NH.

The selenophene compounds of this invention are readily formulated into pharmaceutical compositions, also within the scope of this invention, for use in the presently described method for treatment of patients having tumors, In one preferred embodiment of this invention, the pharmaceutical composition comprises an anti-tumor effective amount of a selenophene compound of formula I:

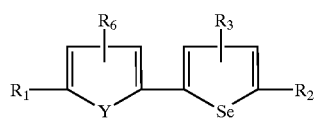

wherein $R_1$ and $R_2$ are independently selected from the group consisting of;

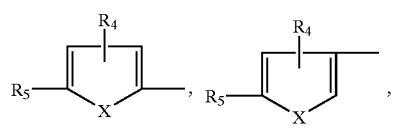

H, CHO, $CH_2OH$ and $CH_2NH_2$,

X and Y are independently selected from the group consisting of Se, S, O and NR, wherein R is H or $C_1$–$C_7$ alkyl $R_3$, $R_4$, $R_5$ and $R_6$ are independently selected from the group consisting of nitro, amino, alkoxy, cyano, chloro, bromo, iodo, $C_1$–$C_7$ alkyl or haloalkyl, $C_1$–$C_7$ alkenyl or haloalkenyl, $C_1$–$C_4$ alkanoyloxy methyl, $CH_2OR_7$, $COR_8$, $CH_2NR_9R_{10}$, $CH(OR_7)R_{11}$, $CH=CR_{12}R_{13}$, $CH=NR_{14}$, $CH_2SC(NH)NH_2$ and $C\equiv CR_{15}$ wherein $R_7$ is H, $CO(CH_2)_2CO_2H$, $(CH_2)_2OCH_3$, $C_1$–$C_4$ alkyl or $COC_1$–$C_{17}$ alkyl;

$R_8$ is H or $C_1$–$C_7$ alkyl;

$R_9$ and $R_{10}$ are independently H, CN, $C_1$–$C_4$ alkyl, or mono- or di-hydroxy$C_2$–$C_4$ alkyl;

$R_{11}$ is $C_1$–$C_7$ alkyl, or $C_1$–$C_7$ alkenyl;

$R_{12}$ and $R_{13}$ are independently H, $C_1$–$C_7$ alkyl, $COOR_8$, CN, $CH(OR_7)COOR_8$, Br, CO-thienyl, $COC_6H_4OH$ (p);

$R_{14}$ is $NR_7$ or $OR_8$;

$R_{15}$ is $COOR_8$, $CH(OR_7)CH_2OR_{16}$ or $CH(OCOC_1$–$C_4$ alkyl)$CH_2OR_8$;

$R_{16}$ is H, $COCH_2CH_2CO_2H$, or $COC_1$–$C_7$ alkyl;

cyclodextrin complexes of such compound and when $R_3$, $R_4$, $R_5$ or $R_6$ is $CH_2NR_6R_7$, the pharmaceutically acceptable salt of the compound represented thereby, and a pharmaceutically acceptable carrier.

Another pharmaceutical composition within the scope of this invention comprises an anti-tumor effective amount of a selenophene compound of the formula I:

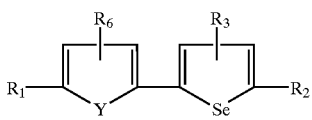

I wherein $R_1$ and $R_2$ are independently selected from the group consisting of;

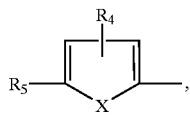

H, CHO, $CH_2OH$ and $CH_2NH_2$;

X and Y are independently selected from the group consisting of Se, S, O $NCH_3$ and NH;

$R_3$, $R_4$ and $R_6$ are H;

$R_5$ is selected from the group consisting of H, CHO, $CH_2OH$ and $CH_2NH_2$; cyclodextrin complexes of such compounds; and when $R_3$, $R_4$, $R_5$ or $R_6$ is $CH_2NH_2$, the pharmaceutically acceptable salt of the compound represented thereby; with the proviso, that when $R_2$ is

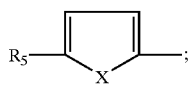

$R_1$ is other than

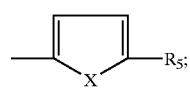

and when $R_1$ is

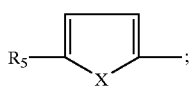

$R_2$ is other than

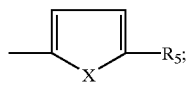

and a pharmaceutically acceptable carrier.

The present compounds are readily prepared using art-recognized chemical-synthesis procedures as exemplified hereinbelow.

The cytotoxic activity of the present selenophene compounds have been measured utilizing two different assays or screens. The first screen measures the cytotoxicity against a panel of sixty different human tumor cell lines. This assay provides data regarding the general cytotoxicity of an individual compound. In particular this type of assay is useful in identifying compounds which have enhanced cytotoxic activity against slow growing tumors as compared to faster growing tumor cells such as leukemia tumor cell lines. The identification of such compounds is critical since previously identified antitumor agents have low cytotoxic activity against slower growing tumors. The specificity of a compound for a limited number of tumor cell lines also indicates that such a compound will likely be less cytotoxic to normal cells. The specificity of a cytotoxic compound for tumor cell lines relative to normal cells is an important characteristic of an effective antitumor agent.

Antitumor cytotoxicity data generated from the National Cancer Institute human tumor cell panels can also be expressed in a graphic pattern (mean graph) to display differential cell growth inhibition (K. D. Paull, R. H. Shoemaker, L. Hodes, A. Monks, D. A. Scudiero, L. Rubinstein, J. Plowman and M. R. Boyd, *J. Natl. Cancer Inst.*, 81, 1088, 1989.) In the mean graph, the arithmetic mean of the logarithm of the $GI_{50}$ (50% growth inhibition), TGI (total growth inhibition) or $LC_{50}$ (50% lethal concentration) values is used as an anchor point. Relative cytotoxicity is displayed by projecting bars to the right or left of the mean, depending on whether cell sensitivity to a test compound is more or less than average. The length of a bar is indicative of differential cytotoxicity against a specific type of tumor cells or tumor panels.

In a second assay, the cytotoxic selectivity is assessed by comparing compound cytotoxicity against human renal carcinoma cells (A-498), ras-transformed human bronchial epithelial cells (TBE) and normal human renal cells (RPTEC). $IC_{50}$ values were compared between treated TBE cells and RPTEC cells and the selective cytotoxicity index (SCI) was determined [SCI=$GI_{50}$(RPTEC)/$GI_{50}$ (A-498)].

The antitumor cytotoxicity of the selenophene compounds tested in those in vitro assays was measured by a microculture assay using either a 3-(4,5-dimethylthiazol-2-yl)-2,5-diphenyltetrazolium bromide (MTT) or sulforhodamine B (SRB) based assay. [M. R. Boyd in "Principles and Practices of Oncology," V. T. DeVita, Jr.]. The experiments were conducted at Purdue University in 96-well microtiter plates and the cytotoxic effects of the selenophene compounds on those cells were measured by cell count using a Coulter Z. F. counter (Hialeah, Fla.). The results are expressed as $GI_{50}$, the concentration of drug at which cell numbers are reduced to 50% of control cell culture [T. C. K. Chan, C. J. Chang, N. M. Koonchanok and R. L. Geahlen, *Biochem. Biophys. Res. Commun.*, 193, 1152, (1993); S. Hellman and S. A. Rosenberg (Eds.), Vol. 3, PPO Updates, Number 10, (1989).]

This in vitro microculture assay has an advantage over in vivo assays in that results are obtained within a week as opposed to several months. The MTT assay is based on the production of a dark blue formazan product by dehydrogenase in the mitochondria of live tumor cells after exposure to drug for 6 days [M. C. Alley, D. A. Scudiero, A. Monks, M. L. Hursey, M. J. Czerwinski, D. L. Fine, B. J. Abbott, J. G. Mayo, R. H. Shoemaker and M. R. Boyd, *Cancer Res.*, 48, 5 89, 1988]. Thus, only live cells are stained and can be measured at 570 nm. The SRB assay is based on the binding of the anionic group to the basic amino acid residues of cellular proteins after exposure of tumor cells to drug for 2 days [ P. Skehan, R. Storeng, D. Scudiero, A. Monks, J. McMahon, D. Vistica, J. T. Warren, H. Bohesch, S. Kenney and M. R. Boyd, *J. Nat. Cancer Inst.*, 82, 1107, 1990.] Thus, the total protein can be measured at 564 nm. Antitumor cytotoxicity is reported as $GI_{50}$, effect drug dose at which cell growth is retarded to 50% of control culture of tumor cells. Thee active compounds are defined as those compounds having $GI_{50}$ values that are less than $10^{-4}$ M or 10 μg/ml.

The data presented in Table 1 illustrates that selenophenes generally exhibit greater cytotoxicity for human renal carcinoma cells in comparison to the normal human cells. The data of Table 1 demonstrates the selective cytotoxicity of various selenophene compounds against human renal carcinoma and ras-oncogene transformed human bronchial epithelial cells [in $GI_{50}$(ug/ml)]. The following abbreviations are used for the tested cell lines:

RPTEC: normal human renal cells

A-498: human renal carcinoma

TBE: ras-transformed human bronchial epithelial cells

SCI: selectively cytotoxicity index=$GI_{50}$ (RPTEC)/$GI_{50}$ (A-498)

TABLE 1

| NSC Number | $GI_{50}$ (μg/ml) | | | |
|---|---|---|---|---|
| | RPTEC | A-498 | TBE | SCI |
| 674973 | $4 \times 10^0$ | $3 \times 10^0$ | $4 \times 10^0$ | 1 |
| 675246 | $1 \times 10^{-1}$ | $3 \times 10^{-6}$ | $3 \times 10^{-3}$ | >1000 |
| | $3 \times 10^{-2}$ | $3 \times 10^{-6}$ | $2 \times 10^{-3}$ | >1000 |
| 675247 | $2 \times 10^{-1}$ | $7 \times 10^{-5}$ | $3 \times 10^1$ | >1000 |
| | $8 \times 10^0$ | $2 \times 10^{-6}$ | $2 \times 10^1$ | >1000 |
| 676628 | $4 \times 10^2$ | $8 \times 10^1$ | $1 \times 10^2$ | 5 |
| 676632 | $2 \times 10^{-3}$ | $3 \times 10^{-7}$ | $<10^{-3}$ | >1000 |
| | $3 \times 10^{-4}$ | $2 \times 10^{-7}$ | $2 \times 10^{-4}$ | >1000 |
| 675347 | $2 \times 10^1$ | $3 \times 10^1$ | $1 \times 10^1$ | <1 |
| 675344 | $<10^{-2}$ | $3 \times 10^{-7}$ | $<10^{-2}$ | >1000 |
| | $1 \times 10^{-4}$ | $6 \times 10^{-8}$ | $7 \times 10^{-6}$ | >1000 |
| 676633 | $2 \times 10^1$ | $1 \times 10^2$ | $1 \times 10^1$ | <1 |
| 676634 | $1 \times 10^1$ | $6 \times 10^{-4}$ | $3 \times 10^{-4}$ | >1000 |
| | $4 \times 10^{-1}$ | $3 \times 10^{-3}$ | $6 \times 10^{-3}$ | >100 |
| 676635 | $2 \times 10^0$ | $<10^{-3}$ | $2 \times 10^1$ | >1000 |
| 123127 | $5 \times 10^{-2}$ | $5 \times 10^{-2}$ | $3 \times 10^{-2}$ | 1 |

NSC Number   Structure

674973   [structure: three linked selenophene rings (Se-Se-Se)]

675246   [structure: three linked selenophene rings with -CH₂OH]

675247   [structure: HOCH₂- three linked selenophene rings -CH₂OH]

TABLE 1-continued

676628   [structure: Se-S-Se linked three-ring]

676632   [structure: HOCH₂- Se-S-Se linked -CH₂OH]

675347   [structure: S-Se-S linked three-ring]

675344   [structure: S-Se-S linked -CH₂OH]

676633   [structure: Se-NH-Se linked three-ring]

676634   [structure: Se-NH-Se linked -CHO]

676635   [structure: Se-NH-Se linked -CH₂OH]

123127   Adriamycin

The present invention further provides pharmaceutical formulations comprising an effective amount of a selenophene compound for treating a patient having a tumor. As used herein, an effective amount of the selenophene compound is defined as the amount of the compound which, upon administration to a patient, inhibits growth of tumor cells, Kills malignant cells, reduces the volume or size of the tumors or eliminates the tumor entirely in the treated patient.

The effective amount to be administered to a patient is typically based on body surface area, patient weight, and patient condition. The interrelationship of dosages for animals and humans (based on milligrams per meter squared of body surface) is described by Freireich, E. J., et al., *Cancer Chemother. Rep.*, 50 (4): 219 (1966). Body surface area may be approximately determined from patient height and weight (see e.g., Scientific Tables, Geigy Pharmaceuticals, Ardley, N.Y., pages 537–538 (1970)). An effective amount of the selenophene compounds in the present invention can range from about 5 mg/kg to about 100 mg/kg, more preferably from about 0.25 mg/kg to about 50 mg/kg, and most preferably about 0.1 to about 10 mg/kg.

Effective doses will also vary, as recognized by those skilled in the art, dependant on route of administration, excipient usage and the possibility of co-usage with other therapeutic treatments including other anti-tumor agents, and radiation therapy.

The pharmaceutical formulation may be administered via the parenteral route, including subcutaneously, intraperitoneally, intramuscularly and intravenously. Examples of parenteral dosage forms include aqueous solutions of the active agent, in a isotonic saline, 5% glucose or other well-known pharmaceutically acceptable liquid carrier. In one preferred aspect of the present embodiment, the selenophene compound is dissolved in a saline solution containing 5% of dimethyl sulfoxide and 10% Cremphor EL (Sigma Chemical Company). Additional solubilizing agents such as cyclodextrins, which form specific, more soluble complexes with the present selenophene compounds, or other solubilizing agents well-known to those familiar with the art, can be utilized as pharmaceutical excipients for delivery of the selenophene compounds.

The present compound can also be formulated into dosage forms for other routes of administration utilizing well-known methods. The pharmaceutical compositions can be formulated, for example, in dosage forms for oral administration in a capsule, a gel seal or a tablet. Capsules may comprise any well-known phannaceutically acceptable material such as gelatin or cellulose derivatives. Tablets may be formulated in accordance with conventional procedure by compressing mixtures of the active polythiophene and solid carriers, and lubricants well-known to those familiar with the art. Examples of solid carriers include starch, sugar, bentonite. The compounds of the present invention can also be administered in a form of a hard shell tablet or capsule containing, for example, lactose or mannitol as a binder and conventional fillers and tableting agents.

The following examples are provided to illustrate various embodiments of Applicants' invention, and are not intended to in any way limit the scope of the invention as set forth in this specification and appended claims.

EXAMPLE 1

Synthesis of α-Terselenophenes

A two-step total synthesis of α-terselenophene from selenophene (Aldrich Chemical Co.) has been developed (See Scheme 1).

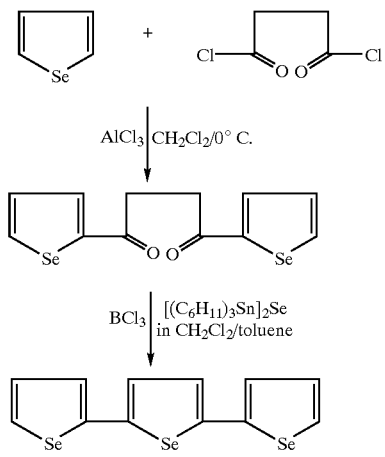

Bis(tricyclohexyltin)selenide can be prepared from tricyclohexyltin chloride (Aldrich Chemical Co.) and sodium selenide (Alfa Chemical Co.). The functional group can be introduced through selective α-formylation using lithium diisopropylamide (LDA) and dimethylformamide (DMF), which can then be sequentially converted into hydroxylmethyl and aminomethyl functional groups. These functional groups can provide required starting points for further chemical modifications, see Scheme 2 as follows:

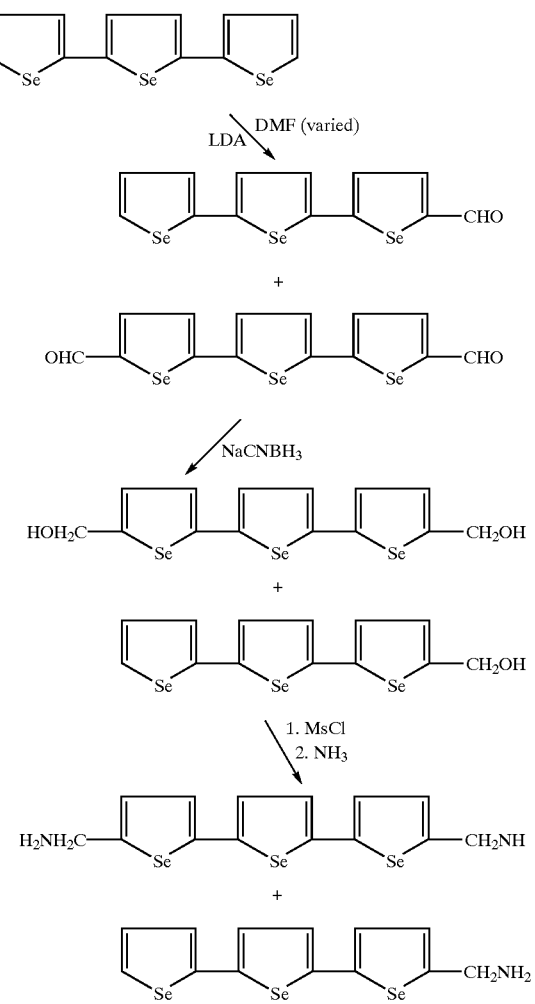

EXAMPLE 2

Synthesis of Hybrid α-Terselenophenes

The synthetic strategy designed for the preparation of α-terselenophene can be readily modified for the synthesis of numerous "hybrid" α-selenophenes containing other five-membered heterocycles (See Scheme 3).

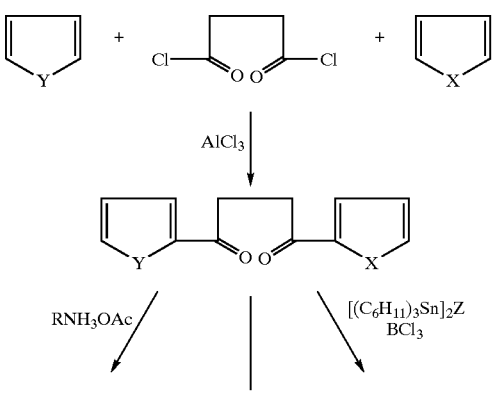

-continued

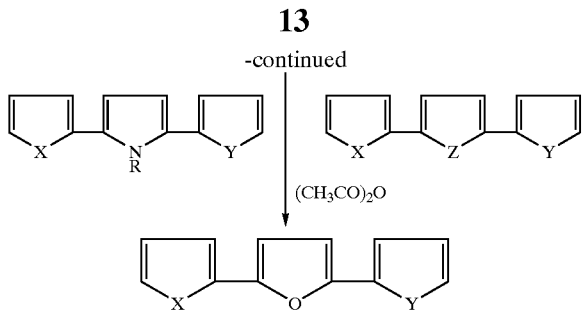

Wherein X, and Y are selected from the group consisting of Se, O, S, NCH₃ and NH₂, and Z is selected from the group consisting of Se, S, NCH₃ and NH₂. Various functional groups can be introduced using the approaches outlined in the synthesis of α-terselenophenes (Scheme 2).

EXAMPLE 3

Preparation of 1,4'-diselenophene-1,4-diketone

A $CH_2Cl_2$ solution containing selenophene (5 g) and succinyl chloride (2 g) was added dropwise to an anhydrous $CH_2Cl_2$ solution (60 mL) containing $AlCl_3$ (5 g) under $N_2$ at 0° C. The reaction mixture was stirred at 0° C. for 1 h, slowly warmed to room temperature, and stirred for 4 h at room temperature. The reaction mixture was poured into a beaker containing ice. Ethyl acetate (200 mL) was added and the organic layer was separated out using a separatory funnel. The aqueous layer was back washed with ethyl acetate (2×100 mL). The combined organic layer was washed with $H_2O$ (2×300 mL). The organic layer was collected, dried over $MgSO_4$, and the solvent was removed under vacuum. The residue was chromatographed over silica gel using (10:1) hexanes/ethyl acetate to afford the product in 25% yield.

EXAMPLE 4

Preparation of 2,2':5',2"-terselenophene

A $BCl_3$ solution (1.0 M solution in hexanes, 580 mL) was added dropwise to an anhydrous toluene solution (5 mL) containing 1,4-diselenophene-1,4-diketone (100 mg) and bis(tricyclohexyltin)selenide (520 mg) under $N_2$ at room temperature. The solution was refluxed for 30 min and cooled to room temperature. The reaction solution was diluted with ethyl acetate (100 mL) and washed with $H_2O$ (2×100 mL). The organic layer was separated, dried over $MgSO_4$, filtered, and the solvent was removed under vacuum, The residue was chromatographed over silica gel using hexanes to afford 2,2':5'2"-terselenophene in 80% yield.

EXAMPLE 5

Preparation of 2-formyl-5,2':5",2"-terselenophene.

LDA (1.0 M solution in THF, 310 mL) was added to an anhydrous THF solution (4 mL) containing 2,2':5',2"-terselenophene (100 mg) under $N_2$ at −78° C. The solution was stirred at −78° C. for 3 h, anhydrous DMF (1 mL) was added, stirred at −78° C. for 1 h, and slowly warmed to room temperature. The reaction solution was diluted with ethyl acetate (100 mL) and washed with $H_2O$ (4×100 mL). The organic layer was separated, dried over $MgSO_4$, filtered, and the solvent was removed under vacuum. The residue was chromatographed over silica gel using $CH_2Cl_2$ to afford 2-formyl-5,2':5',2"-terselenophene in 75% yield.

EXAMPLE 6

Preparation of 2,5"-diformyl-5,2':5',2"-terselenophene

LDA (1.0 M solution in THF, 1.0 mL) was added to an anhydrous THF solution (4 mL) containing 2,2':5',2"-terselenophene (100 mg) under $N_2$ at −78° C. The solution was stirred at −78° C. for 3 h, anhydrous DMF (2 mL) was added, stirred at −78° C. for 1 h, and slowly warmed to room temperature. The reaction solution was diluted with ethyl acetate (100 mL) and washed with $H_2O$ (4×100 mL). The organic layer was separated, dried over $MgSO_4$, filtered, and the solvent was removed under vacuum. The residue was chromatographed over silica gel using (5:1) $CH_2Cl_2$/ethyl acetate to afford 2,5"-diformyl-5,2':5',2"-terselenophene in 75% yield.

EXAMPLE 7

Preparation of 2-hydroxymethyl-5,2':5',2"-terselenophene $NaBH_4$ (10 mg) was added to a THF solution (2 mL) 2-formyl-5,2':5',2"-terselenophene (15 mg) and stirred at room temperature for 2 h. The reaction solution was diluted with ethyl acetate (50 mL), washed with 2N HCl (5 mL), and then washed with $H_2O$ (3×50 mL). The organic layer was separated, dried over $MgSO_4$, filtered, and the solvent was removed under vacuum. The residue was chromatographed over silica gel using (2:1) hexanes/ethyl acetate to afford 2-hydroxymethyl-5,2':5',2"-terselenophene in 98% yield.

EXAMPLE 8

Preparation of 2,5"-dihydroxymethyl-5,2':5',2"-terselenophene $NaBH_4$ (10 mg) was added to a THF solution (2 mL) containing 2,5"-diformyl-5,2':5',2"-terselenophene (15 mg) and stirred at room temperature for 5 h. The reaction solution was diluted with ethyl acetate (50 mL), washed with 2N HCl (5 mL), and washed with $H_2O$ (3×100 mL). The organic layer was separated, dried over $MgSO_4$, filtered, and the solvent was removed under vacuum. The residue was chromatographed over silica gel using (1:1) hexanes/ethyl acetate to afford 2,5"-dihydroxymethyl-5,2':5',2"-terselenophene in 98% yield.

EXAMPLE 9

Preparation of 2,4-diselenophenylfuran d-10-camphorsulfonic acid (2 g) was added to an ethanolic solution (15 mL) containing 2',2"-diselenophene-1,4-diketone (100 mg) and refluxed for 2 days. The reaction solution was diluted with ethyl acetate (100 mL) and washed with $H_2O$ (3×100 mL). The organic layer was separated, dried over $MgSO_4$, filtered, and the solvent was removed under vacuum. The residue was chromatographed over silica gel using (10:1) hexanes/ethyl acetate to afford 2,2':5,2"-diselenophenylfuran in 90% yield.

EXAMPLE 10

Preparation of 5'-formyl-2,2':5,2"-diselenophenylfuran

LDA (1 molar solution in THF, 00 mL) was added to an anhydrous THF solution (00 mL) containing 2,2':5,2"- diselenophenylfuran (00 mg) under $N_2$ at −78° C. The solution was stirred at −78° C. for 3 h, anhydrous DMF (excess) was added, stirred at −78° C. for 1 h, and slowly warmed to room temperature. The reaction solution was diluted with ethyl acetate (00 mL) and washed with $H_2O$ (3×100 mL). The organic layer was separated, dried over $MgSO_4$, filtered, and the solvent was removed under vacuum. The residue was chromatographed over silica gel using (4:1) hexanes/ethyl acetate to afford 5'-formyl-2,2':5,2"-diselenophenylfuran in 00% yield.

EXAMPLE 11

Preparation of 5',5"-diformyl-2,2':5,2"-diselenophenylfuran

LDA (1 molar solution in THF, 00 mL) was added to an anhydrous THF solution (00 mL) containing 2,2':5,2"-diselenophenylfuran (00 mg) under $N_2$ at −78° C. The solution was stirred at −78° C. for 3 h, anhydrous DMF (excess) was added, stirred at −78° C. for 1 h, and slowly warmed to room temperature. The reaction solution was diluted with ethyl acetate (00 mL) and washed with $H_2O$ (3×100 mL). The organic layer was separated, dried over $MgSO_4$, filtered, and the solvent was removed under vacuum. The residue was chromatographed over silica gel using (4:1) hexanes/ethyl acetate to afford 5,5"-diformyl-2,2':5,2"-diselenophenylfuran in 00% yield.

EXAMPLE 12

Preparation of 5'-hydroxymethyl-2,2':5,2"-diselenophenylfuran $NaBH_4$ (excess) was added to a THF solution (00 mL) containing 5'-formyl-2,2':5,2"-diselenophenylfuran (00 mg) and stirred at room temperature for 5 h. The reaction solution was diluted with ethyl acetate (100 mL) and washed with $H_2O$ (3×100 mL). The organic layer was separated, dried over $MgSO_4$, filtered, and the solvent was removed under vacuum. The residue was chromatographed over silica gel using (2:1) hexanes/ethyl acetate to afford 5'-hydroxymethyl-2,2':5,2"-diselenophenylfuran in 00% yield.

EXAMPLE 13

Preparation of 5',5"-dihydroxymethyl-2,2':5,2"-diselenophenylfuran $NaBH_4$ (excess) was added to a THF solution (00 mL) containing 5',5"-diformyl-2,2':5,2"-diselenophenylfuran (00 mg) and stirred at room temperature for 5 h. The reaction solution was diluted with ethyl acetate (100 mL) and washed with $H_2O$ (3×100 mL). The organic layer was separated, dried over $MgSO_4$, filtered, and the solvent was removed under vacuum. The residue was chromatographed over silica gel using (1:1) hexanes/ethyl acetate to afford 5',5"-dihydroxymethyl-2,2':5,2"-diselenophenylfuran in 00% yield.

EXAMPLE 14

Preparation of 2,2':5,2"-diselenophenylthiophene $BCl_3$ (1.0 M solution in hexanes, 580 mL) was added dropwise to an anhydrous toluene solution (5 mL) containing 2',2"-diselenophenyl-1,4-diketone (100 mg) and bis(tricyclohexyltin)sulfide (520 mg) under $N_2$ at room temperature. The solution was refluxed for 30 min and cooled to room temperature. The reaction solution was diluted with ethyl acetate (100 mL) and washed with $H_2O$ (2×100 mL). The organic layer was separated, dried over $MgSO_4$, filtered, and the solvent was removed under vacuum. The residue was chromatographed over silica gel using hexanes to afford 2,2':5,2"-diselenophenylthiophene in 85% yield.

EXAMPLE 15

Preparation of 5'-formyl-2,2':5,2"-diselenophenylthiophene

LDA (1.0 M solution in THF, 350 mL) was added to an anhydrous THF solution (4 mL) containing 2,2':5,2"-diselenophenylthiophene under $N_2$ at −78° C. The solution was stirred at −78° C. for 3 h, anhydrous DMF (1 mL) was added, stirred at −78 ° C. for 1 h, and slowly warmed to room temperature. The reaction solution was diluted with ethyl acetate (50 mL) and washed with $H_2O$ (3×100 mL). The organic layer was separated, dried over $MgSO_4$, filtered, and the solvent was removed under vacuum. The residue was chromnatographed over silica gel using $CH_2Cl_2$ to afford 5'-formyl-2,2':5,2"-diselenophenylthiophene in 80% yield.

EXAMPLE 16

Preparation of 5',5"-diformyl-2,2':5,2"-diselenophenylthiophene

LDA (1.0 M solution in THF, 1 mL) was added to an anhydrous THF solution (4 mL) containing 2,2':5,2"-diselenophenylthiophene under $N_2$ at −78° C. The solution was stirred at −78° C. for 3 h, anhydrous DMF (2 mL) was added, the solution was stirred at −78° C. for 1 h, and slowly warmed to room temperature. The reaction solution was diluted with ethyl acetate (100 mL) and washed with $H_2O$ (3×100 mL). The organic layer was separated, dried over $MgSO_4$, filtered, and the solvent was removed under vacuum. The residue was chromatographed over silica gel using (5:1) $CH_2Cl_2$/ethyl acetate to afford 5',5"-diformyl-2,2':5,2"-diselenophenylthiophene in 80% yield.

EXAMPLE 17

Preparation of 5'-hydroxymethyl-2,2':5,2"-diselenophenylthiophene $NaBH_4$ (10 mg) was added to a THF solution (3 mL) containing 5'-formyl-2,2':5,2"-diselenophenylthiophene (20 mg) and stirred at room temperature for 2 h. The reaction solution was diluted with ethyl acetate (50 mL) and washed with $H_2O$ (5×50 mL). The organic layer was separated, dried over $MgSO_4$, filtered, and the solvent was removed under vacuum. The residue was chromatographed over silica gel using (2:1) $CH_2Cl_2$/ethyl acetate to afford 5'-hydroxymethyl-2,2':5,2"-diselenophenylthiophene in 98% yield.

EXAMPLE 18

Preparation of 5,5"-dihydroxymethyl-2,2':5,2"-diselenophenylthiophene $NaBH_4$ (10 mg) was added to a THF solution (3 mL) containing 5',5"-diformyl-2,2':5,2"-diselenophenylthiophene (20 mg) and stirred at room temperature for 5 h. The reaction solution was diluted with ethyl acetate (50 mL) and washed with $H_2O$ (5×50 mL). The organic layer was separated, dried over $MgSO_4$, filtered, and the solvent was removed under vacuum. The residue was chromatographed over silica gel using (1:1) hexanes/ethyl acetate to afford 5',5"-dihydroxymethyl-2,2':5,2"-diselenophenylthiophene in 98% yield.

EXAMPLE 19

Preparation of 2,2':5,2"-diselenophenylpyrrole

An ethanolic solution (20 mL) containing 2',2"-diselenophenyl-1,4-diketone (200 mg) and ammonium acetate (500 mg) and sodium acetate (200 mg) was refluxed overnight. The reaction solution was diluted with ethyl acetate (100 mL) and washed with $H_2O$ (3×100 mL). The organic layer was separated, dried over $MgSO_4$, filtered, and the solvent was removed under vacuum. The residue was chromatographed over silica gel using (10:1) hexanes/ethyl acetate to afford 2,2':5,2"-diselenophenylpyrrole in 94% yield.

EXAMPLE 20

Preparation of 5'-formyl-2,2':5,2"-diselenophenylpyrrole

LDA (1.0 M solution in THF, 760 mL) was added to an anhydrous THF solution (5 mL) containing 2,2':5,2"-diselenophenylpyrrole (100 mg) under $N_2$ at −78° C. The solution was stirred at −78° C. for 3 h, anhydrous DMF (1.5 mL) was added, the solution was slowly warmed to room temperature, and stirred at room temperature for 2 h. The reaction solution was diluted with ethyl acetate (100 mL) and washed with $H_2O$ (3×100 mL). The organic layer was separated, dried over $MgSO_4$, filtered, and the solvent was removed under vacuum. The residue was chromatographed over silica gel using (3:1) hexanes/ethyl acetate to afford 5'-formyl-2,2':5,2"-diselenophenylpyrrole in 75% yield.

EXAMPLE 21

Preparation of 5'-hydroxymethyl-2,2':5,2"-diselenophenylpyrrole $NaBH_4$ (20 mg) was added to a THF solution (2 mL) containing 5'-formyl-2,2':5,2"-diselenophenylpyrrole (20 mg) and stirred at room temperature for 2 h. The reaction solution was diluted with ethyl acetate (50 mL) and washed with $H_2O$ (3×50 mL). The organic layer was separated, dried over $MgSO_4$, filtered, and the solvent was removed under vacuum. The residue was chromatographed over silica gel using (2:1) hexanes/ethyl acetate to afford 5'-hydroxymethyl-2,2':5,2'-diselenophenylpyrrole in 98% yield.

EXAMPLE 22

Preparation of 2',2"-difuranyl-1,4-diketone

A $CH_2Cl_2$ solution containing furan (10 mL) and succinyl chloride (2 g) was added dropwise to an anhydrous $CH_2Cl_2$ solution (100 mL) containing $AlCl_3$ (10 g) under $N_2$ at 0° C. The reaction mixture was stirred at 0° C. for 2 h, slowly warmed to room temperature, and stirred for 4 h. The reaction mixture was poured into a beaker containing ice. Ethyl acetate (300 mL) was added and the organic layer was separated out using a separatory funnel. The aqueous layer was back washed with ethyl acetate (2×100 mL). The combined organic layer was washed with $H_2O$ (2×300 mL). The organic layer was collected, dried over $MgSO_4$, and the solvent was removed under vacuum. The residue was chromatographed over silica gel using (3:1) hexanes/ethyl acetate to afford 2',2"-difuranyl-1,4-diketone in 25% yield.

EXAMPLE 23

Preparation of 2,2':5,2"-difuranylselenophene $BCl_3$ (1.0 M solution in hexanes, 900 mL) was added dropwise to an anhydrous toluene solution (00 mL) containing 2',2"-difuranyl-1,4-diketone (100 mg) and bis (tricyclohexyltin)-selenide (750 mg) under $N_2$ at room temperature. The solution was refluxed for 30 min and cooled to room temperature. The reaction solution was diluted with ethyl acetate (100 mL) and washed with $H_2O$ (2×100 mL). The organic layer was separated, dried over $MgSO_4$, filtered, and the solvent was removed under vacuum. The residue was chromatographed over silica gel using hexanes to afford 2,2':5,2"-difuranylselenophene in 80% yield.

EXAMPLE 24

Preparation of 5'-formyl-2,2':5,2"-difuranylselenophene

LDA (1.0 M solution in THF, 420 mL) was added to an anhydrous THF solution (4 mL) containing 2,2':5,2"-difuranylselenophene (100 mg) under $N_2$ at −78° C. The solution was stirred at −78° C. for 3 h, anhydrous DMF (1 mL) was added, the solution was stirred at −78° C. for 1 h, and slowly warmed to room temperature. The reaction solution was diluted with ethyl acetate (100 mL) and washed with $H_2O$ (3×100 mL). The organic layer was separated, dried over $MgSO_4$, filtered, and the solvent was removed under vacuum. The residue was chromatographed over silica gel using (3:1) hexanes/ethyl acetate to afford 5'-formyl-2, 2':5,2"-difuranylselenophene in 75% yield.

EXAMPLE 25

Preparation of 5',5"-diformyl-2,2':5,2"-difuranylselenophene

LDA (1.0 M solution in THF, 00 mL) was added to an anhydrous THF solution (4 mL) containing 2,2':5,2"-difuranylselenophene (100 mg) under $N_2$ at −78° C. The solution was stirred at −78° C. for 3 h, added anhydrous DMF (2 mL), stirred at −78 ° C. for 1 h, and slowly warmed to room temperature. The reaction solution was diluted with ethyl acetate (100 mL) and washed with $H_2O$ (3×100 mL). The organic layer was separated, dried over $MgSO_4$, filtered, and the solvent was removed under vacuum. The residue was chromatographed over silica gel using (2:1) hexanes/ethyl acetate to afford 5',5"-diformyl-2,2':5,2"-difuranylselenophene in 80% yield.

EXAMPLE 26

Preparation of 5'-hydroxymethyl-2,2':5,2"-difuranylselenophene $NaBH_4$ (10 mg) was added to a THF solution (2 mL) containing 5'-formyl-2,2':5,2"-difuranylselenophene (20 mg) and stirred at room temperature for 5 h. The reaction solution was diluted with ethyl acetate (50 mL) and washed with $H_2O$ (3×50 mL). The organic layer was separated, dried over $MgSO_4$, filtered, and the solvent was removed under vacuum. The residue was chromatographed over silica gel using (2:1) hexanes/ethyl acetate to afford 5'-hydroxymethyl-2,2':5,2"-difuranylselenophene in 98% yield.

EXAMPLE 27

Preparation of 5',5"-dihydroxymethyl-2,2':5,2"-difuranylselenophene

NaBH$_4$ (10 mg) was added to a THF solution (2 mL) containing 5',5"-diformyl-2,2':5,2"-difuranylselenophene (20 mg) and stirred at room temperature for 5 h. The reaction solution was diluted with ethyl acetate (50 mL) and washed with H$_2$O (3×50 mL). The organic layer was separated, dried over MgSO$_4$, filtered, and the solvent was removed under vacuum. The residue was chromatographed over silica gel using (1:1) hexanes/ethyl acetate to afford 5',5"-dihydroxymethyl-2,2':5,2"-difuranylselenophene in 98% yield.

EXAMPLE 28

Preparation of 2',2"-dithienyl-1,4-diketone

A CH$_2$Cl$_2$ solution containing thiophene (10 mL) and succinyl chloride (2 g) was added dropwisely to an anhydrous CH$_2$Cl$_2$ solution (100 mL) containing AlCl$_3$ (10 g) under N$_2$ at 0° C. The reaction mixture was stirred at 0° C. for 2 h, slowly warmed to room temperature, and stirred for 4 h. The reaction mixture was poured into a beaker containing ice. Ethyl acetate (300 mL) was added and the organic layer was separated out using a separatory funnel. The aqueous layer was back washed with ethyl acetate (2×100 mL). The combined organic layer was washed with H$_2$O (2×300 mL). The organic layer was collected, dried over MgSO$_4$, and the solvent was removed under vacuum. The residue was chromatographed over silica gel using (3:1) hexanes/ethyl acetate to afford 2',2"-dithienyl-1,4-diketone in 25% yield.

EXAMPLE 29

Preparation of 2,2':5,2"-dithienylselenophene

BCl$_3$ (1.0 M solution in hexanes, 1.6 mL) was added dropwise to an anhydrous toluene solution (5 mL) containing 2',2"-dithienyl-1,4-diketone (200 mg) and bis(tricyclohexyltin)selenide (1.3 g) under N$_2$ at room temperature. The solution was refluxed for 30 min and cooled to room temperature. The reaction solution was diluted with ethyl acetate (100 mL) and washed with H$_2$O (3×100 mL). The organic layer was separated, dried over MgSO$_4$, filtered, and the solvent was removed under vacuum. The residue was chromatographed over silica gel using hexanes to afford 2,2':5,2"-dithienylselenophene in 90% yield.

EXAMPLE 30

Preparation of 5'-formyl-2,2':5,2"-dithienylselenophene

LDA (1.0 M solution in THF, 380 mL) was added to an anhydrous THF solution (4 mL) containing 2,2':5,2"-dithienylselenophene (100 mg) under N$_2$ at −78° C. The solution was stirred at −78° C. for 3 h, anhydrous DMF (1 mL) was added, the solution stirred at −78° C. for 1 h, and slowly warmed to room temperature. The reaction solution was diluted with ethyl acetate (100 mL) and washed with H$_2$O (3×100 mL). The organic layer was separated, dried over MgSO$_4$, filtered, and the solvent was removed under vacuum. The residue was chromatographed over silica gel using (3:1) hexanes/ethyl acetate to afford 5'-formyl-2,2':5,2"-dithienylselenophene in 75% yield.

EXAMPLE 31

Preparation of 5',5"-diformyl-2,2':5,2"-dithienylselenophene

LDA (1.0 M solution in THF, 1.0 mL) was added to an anhydrous THF solution (4 mL) containing 2,2':5,2"-dithienylselenophene (100 mg) under N$_2$ at −78° C. The solution was stirred at −78° C. for 3 h, anhydrous DMF (2 mL) was added, the solution stirred at −78° C. for 1 h, and slowly warmed to room temperature. The reaction solution was diluted with ethyl acetate (100 mL) and washed with H$_2$O (3×100 mL). The organic layer was separated, dried over MgSO$_4$, filtered, and the solvent was removed under vacuum. The residue was chromatographed over silica gel using (2:1) hexanes/ethyl acetate to afford 5',5"-diformyl-2,2':5,2"-dithienylselenophene in 85% yield.

EXAMPLE 32

Preparation of 5'-hydroxymethyl-2,2':5,2"-dithienylselenophene

NaBH$_4$ (10 mg) was added to a THF solution (2 mL) containing 5'-formyl-2,2':5,2"-dithienylselenophene (20 mg) and stirred at room temperature for 5 h. The reaction solution was diluted with ethyl acetate (50 mL) and washed with H$_2$O (3×50 mL). The organic layer was separated, dried over MgSO$_4$, filtered, and the solvent was removed under vacuum. The residue was chromatographed over silica gel using (2:1) hexanes/ethyl acetate to afford 5'-hydroxymethyl-2,2':5,2"-dithienylselenophene in 98% yield.

EXAMPLE 33

Preparation of 5',5"-dihydroxymethyl-2,2':5,2"-dithienylselenophene

NaBH$_4$ (10 mg) was added to a THF solution (2 mL) containing 5',5"-diformyl-2,2':5,2"-dithienylselenophene (20 mg) and stirred at room temperature for 5 h. The reaction solution was diluted with ethyl acetate (50 mL) and washed with H$_2$O (3×50 mL). The organic layer was separated, dried over MgSO$_4$, filtered, and the solvent was removed under vacuum. The residue was chromatographed over silica gel using (1:1) hexanes/ethyl acetate to afford 5',5"-dihydroxymethyl-2,2':5,2"-dithienylselenophene in 98% yield.

EXAMPLE 34

Alternative Method of Synthesizing Hybrid α-Terselenophenes

In addition to the method of synthesis described in Example 2, an alternative synthesis strategy (Scheme 4) can be utilized to prepare numerous "hybrid" α-Terselenophenes.

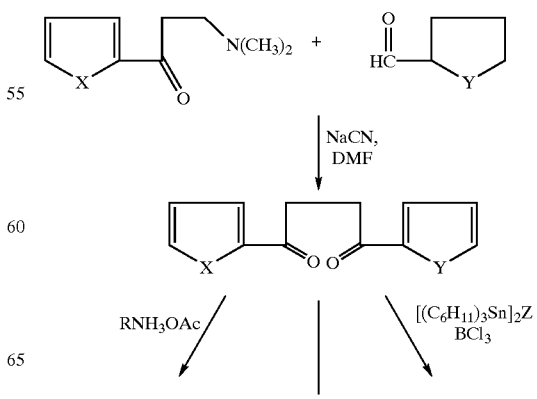

-continued

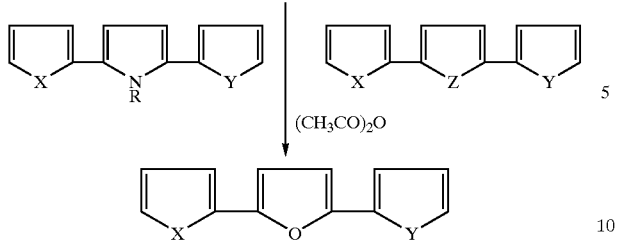

Wherein X, and Y are selected from the group consisting of Se, O, S, N(CH$_3$)$_2$ and NH$_2$, and Z is selected from the group consisting of Se, S, N(CH$_3$)$_2$ and NH$_2$. Various functional groups can be introduced using the approaches outlined in the synthesis of α-terselenophenes (Scheme 2).

EXAMPLE 35

Preparation of 3-Dimethylamino-1-(2'-selenyl) propanone

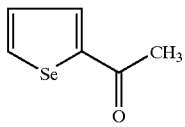

1

Synthesis of 2-acetylselenophene(1): A solution of selenophene (2.0 g, 15 mmol), acetic anhydride (2.34 g, 23 mmol) and tin (IV) chloride (0.06 g, 0.23 mmol) in 30 mL of dry methene chloride was stirred under Argon for two days until TLC plate showed completion of the reaction.

A mixture of crude 2-acetylselenophene (2.6 g, 15 mmol), paraformaldehyde (0.59 g, 19.6 mmol), dimethylamine hydrochloride (1.6 g, 19.5 mmol) and 0.15 mL of HCl was refluxed for 16 h in 7 mL of ethanol. The reaction mixture was cooled and the precipitate was filtered, washed with ether and dried; yield 2.77 g (69.3%). This Mannich base hydrochloride (2 g) was basified using ammonium hydroxide. The solution was extracted (3×15 mL) with diethyl ether. The organic layer was washed with water and dried with sodium sulfate. Evaporation of ether gave 1.6 g of product 2.

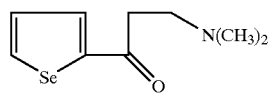

2

$^1$H NMR (CDCl$_3$) δ8.37 (dd, 1H, H-5 of selenophene ring, J=5.52, 0.99), 7.95 (dd, 1H, H-3 of selenophene ring, J=0.99, 3.99), 7.40 (dd, 1H, H-4 of selenophene ring, J=5.52, 3.99), 3.10 (t, 2H, CO—CH$_2$, J=7.6), 2.76 (t, 2H, CH$_2$—NMe$_2$, J=7.6), 2.29 (s, 6H, NMe$_2$).

EXAMPLE 36

Preparation of 1-(2'-Thienyl)-4-(2"-selenyl)butane-1,4-dione(3)

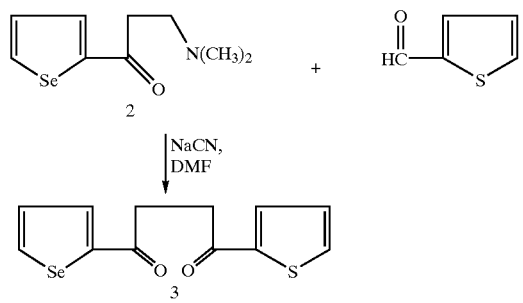

A solution of 2-formylthiophene (1.05 g, 9.4 mmol) in 4 mL dry DMF was added to a suspension of sodium cyanide (0.16 g, 3.4 mmol) in 4 mL, dry DMF After stirring for 10 min, the 3-dimethylamino-1-(2'-selenyl)propanone 2 (1.73 g, 7.52 mmol) in 10 mL DMF was added slowly. The mixture was stirred overnight. Water was added (30 ML), and the product was extracted with chloroform (3×30 mL). The extract was washed with water, dried over sodium sulfate, and evaporated. The product 3 was recrystallized from ethanol; yield: 1.97 g (88.3%). mp: 121–122.40° C. $^1$H NMR (500 MHz, CDCl$_3$) δ8.37 (dd, 1H, H-5 of selenophene ring, J=5.46, 0.91), 8.03 (dd, 1H, H-3 of selenophene ring, J=3.92, 0.91), 7.81 (dd, 1H, H-5 of thiophene ring, J=0.94, 3.82), 7.63 (dd, 1H, H-3 of thiophene ring, J=4.91,0.94), 7.40 (dd, 1H, H-4 selenophene ring, J=5.46, 0.91), 7.14,(dd, 1H, H-4 of thiophene ring, J=3.82, 4.91), 3.40 (m, 4H, CH$_2$—CH$_2$). Anal. Calcd. for C$_{12}$H$_{10}$O$_2$SSe:C, 48.49; H, 3.39; S, 10.79. Found: C, 48.83; H, 3.38; S, 10.46.

EXAMPLE 37

Preparation of 2-(2'-Selenyl)-5-(2"-thienyl) thiophene (4)

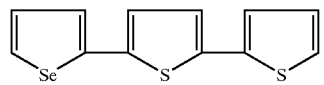

4

1-(2'-Thienyl)-4-(2"-selenyl)butane-1,4-dione 3 (1.1 g, 3.70 mmol) and Lawesson's reagent (0.99 g, 2.44 mmol) were refluxed overnight in 15 mL toluene. The toluene was evaporated and the crude product was purified using silica flash column with ether/hexane as eluent. The product 4 was recrystallized from methanol; yield: 0.9 g (82.3%). mp. 103–104° C. $^1$H NMR (CDCl$_3$) 67 7.84 (dd, 1H, J=5.57, 1.04), 7.30 (dd 1H, J=3.78, 1.04), 7.20 (m, 2H), 7.15 (dd, 1H, J=3.52, 1.1), 7.00 (m, 3H); $^{13}$C NMR (300 Mhz, CDCl$_3$) δ142.09 (weak), 138.36 (weak), 137.01 (weak), 136.32 (weak), 130.29, 129.60, 127.84, 125.73, 124.96, 124.45, 124.29, 123.63. Anal. Calcd for C$_{12}$H$_8$S$_2$Se: C, 48.81; H, 2.73; S, 21.72. Found: C, 49.19; H, 2.58; S, 21.68.

EXAMPLE 38

Preparation of 2-(2'-Selenyl)-5-(2"-thienyl)furene (5)

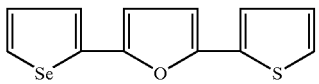

1-(2'-Thienyl)-4-(2"-selenyl)butane-1,4-dione 3 (0.76 g, 2.56 mmol) was added to 35 mL of acetic anhydride, then slowly added 3.0 ml of HCl After 4 h at room temperature, the reaction mixture was poured into ice water and extracted with ether. The organic layer was washed with $NaHCO_3$ and water, dried over sodium sulfate. After evaporation of the solvent, the crude material was subjected to silica column purification to give the product 5. Yield: 0.51 g (75.5%). The yellowish white solid was recrystallized from methanol. mp. 85–87° C. $^1$H NMR ($CDCl_3$) δ7.89 (dd, 1H, J=4.51, 1.03), 7.44 (dd, 1H, J=3.82, 1.01), 7.29(dd, 1H, J=3.72, 1.08), 7.26 (dd, 1H, J=4.51, 3.82), 7.22 (dd, 1H, J=5.03, 1.08), 7.03 (dd, 1H, J=5.02, 3.70), 6.53 (m, 2H).

EXAMPLE 39

Preparation of 2-(2'-Selenyl)-5-(2"-thienyl)pyrrol (6)

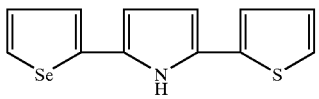

1-(2'-Thienyl)-4-(2"-selenyl)butane-1,4-dione 3 (0.4 g, 1.35 mmol), sodium acetate (0.33 g, 4.0 mmol) and ammonium acetate (0.78 g, 10.1 mmol) were refluxed at 95° C. overnight in 20 mL ethanol. The solvent was evaporated and the crude product 6 was purified using silica flash column with ether/hexane as eluent; yield: 0.27 g (73%). mp. 82–83.5° C. $^1$H NMR δ8.26 (br, 1H), 7.81 (d, 1H, J=5.27), 7.25 (dd, 1H, J=3.78, 5.27), 7.20 (d, 1H, J=3.78), 7.16 (d, 1H, J=5.01), 7.07 (d, 1H, J=3.60), 7.02 (dd, 1H, J=5.01, 3.60), 6.40 (m, 2H).

EXAMPLE 40

Preparation of 1-(2'-Selenyl)-4-(2"-furyl)butane-1,4-dione (7)

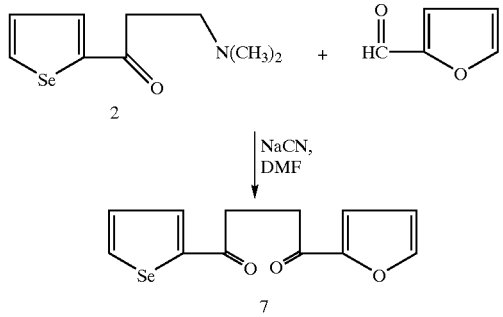

A solution of 2-formylfurene (2.27 g, 23.65 mmol) in 20 mL dry DMF was added to a suspension of sodium cyanide (0.42 g, 8.45 mmol) in 10 mL dry DMF After stirring for 10 min, 3-dimethylamino-1-(2'-selenyl)propanone 2 (4.3 g, 18.8 mmol) in 20 mL DMF was added slowly. The mixture was stirred overnight. Water was added (100 mL), and the product was extracted with chloroform (3×100 mL). The extract was washed with water, dried over sodium sulfate, and evaporated. The product 7 was recrystallized from ethanol; yield: 3.52 g (66.7%). mp. 82–83.5° C. $^1$H NMR ($CDCl_3$) δ8.35 (dd, 1H, H-5 of selenophene ring, J=5.51, 0.78), 8.01 (dd, 1H, H-3 of selenophene ring, J=3.99, 0.79), 7.58 (d, 1H, H-5 of furene ring, J=1.71), 7.39 (dd, 1H, H-4 of selenophene ring, J=5.52, 3.99), 7.23 (d, 1H, H-3 of furene ring, J=3.54), 6.53 (dd, 1H, H-4 of furene ring, J=3.54, 1.70), 3.33 (m, 4H, $CH_2$—$CH_2$).

EXAMPLE 41

Preparation of 2-(2'-Selenyl)-5-(2"-furyl)thiophene (8)

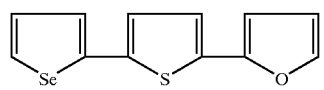

1-(2'-Selenyl)-4-(2"-furyl)butane-1,4-dione 7 (0.25 g, 0.9 mmol) and Lawesson's reagent (0.66 g, 1.63 mmol) were refluxed overnight in 7 mL toluene. The toluene was evaporated and the crude product was purified using silica flash column. with ether/hexane as eluent. The product 8 was recrystallized from methanol; yield: 0.22 g (88%). mp. 76–77° C. $^1$H NMR δ7.86 (dd, 1H, J=5.58, 1.00), 7.40 (d, 1H, J=1.76), 7.31(dd, 1H, J=3.87, 1.00), 7.23 (dd, 1H, J=5.59, 3.87), 7.11 (d, 1H, J=3.78), 7.03 (d, 1H, J=3.81), 6.49 (d, 1H, J=3.36), 6.43(dd, 1H, J=1.77, 3.36).

EXAMPLE 42

Preparation of 2-(2'-Selenyl)-5-(2"-furyl)pyrroI (9)

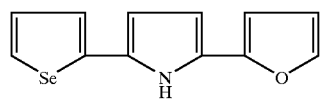

1-(2'-Thienyl)-4-(2"-furyl)butane-1,4-dione 7 (0.20 g, 0.71 mmol), sodium acetate (0.18 g, 2,1 mmol) and ammonium acetate (0.41 g, 5.3 mmol) were refluxed at 95° C. overnight in 12 mL ethanol. The solvent was evaporated and the crude product 9 was purified using silica flash column with ether/hexane as eluent, yield: 0.15 g (80%). mp. 73–74° C. $^1$HNMR δ8.50 (br, 1H), 7.80 (d, 1H, J=5.45), 7.36 (dd, 1H, J=1.02, 0.78), 7.22(m, 2H), 6.40 (in, 4H).

EXAMPLE 43

Preparation of 1,4-Bis-(2'-selenyl)butane-1,4-dione (11)

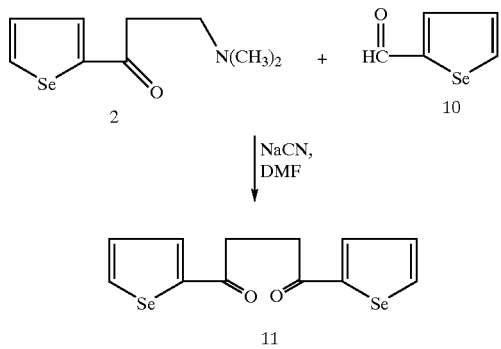

Synthesis of 2-formylselenophene (10): A solution of selenophene (1.31 g, 10 mmol) in 10 ml dichloroethane was added to a mixture of freshly distilled phosphorus oxychloride (2.0 g, 13 mmol) and DMF (1.10 g, 15 mmol). After stirring for 12 hr at 60° C., 2 ml water solution of sodium acetate (2.04 g, 15 mmol) was added to the reaction mixture, and the mixture was allowed to react for another hour. Water was added (20 mL), and the product was extracted with dichloromethane (3×20 mL). The extract was washed with water, dried over sodium sulfate, and carefully evaporated.

A solution of crude 2-formylselenophene (454 mg, 2.9 mmol) in 0.6 mL dry DMF was added to a suspension of sodium cyanide (34.3 mg, 0.7 mmol) in 0.4 mL dry DMF. After stirring for 5 min, the Mannich base, 3-dimethylamino-1-(2-selenyl)-propanone 2 (368 mg, 1.6 mmol) in 1.2 mL DMF was added slowly. The mixture was stirred overnight. Water was added (4 mL, and the product was extracted with dichloromethane (3×6 mL). The extract was washed with water, dried over sodium sulfate, and evaporated. The product was purified from silica gel chromatography with THF/hexane as eluent. Yield: 105 mg (20%). $^1$HNMR (CDCl$_3$) δ8.37 (dd, 1Hx2, H-5 of selenophene ring, J=5.53, 1.01), 8.02 (dd, 1Hx2, H-3 of selenophene ring, J=1.00, 3.97), 7.40 (dd, 1Hx2, H-4 of selenophene ring, J=3.97, 5.50), 3.39 (s, 2Hx2, CH$_2$—CH$_2$).

EXAMPLE 44

Preparation of 2,5-Bis-(2'-selenyl)-N-methylpyrrol (12)

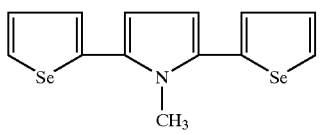

1,4-Bis-(2'-selenyl)butane-1,4-dione 11 (34.4 mg, 0.1 mmol), sodium acetate (123 mg, 0.15 mmol) and methylamine chloride (101.3 mg, 0.15 mmol) were refluxed overnight in 3 mL ethanol. 10 ml water was then added, and the product was extracted with dichloromethane. The product 12 was recrystallized from ethanol; yield: 26 mg (76%). $^1$H NMR (CDCl$_3$) δ7.96 (dd, 1Hx2, H-5 of selenophene ring J=5.64, 1.64), 7.31 (dd, 1Hx2, H-4 of selenophene ring J=5.64, 3.78), 7.20 (dd, 1Hx2, H-3 of selenophene ring J=3.78, 1.64), 6.32 (s, 1Hx2, H-¾ of pyrrol ring), 3.74 (s, 3H, N-Me).

EXAMPLE 45

Preparation of 2,5-Bis-(2'-thienyl)selenophene (13)

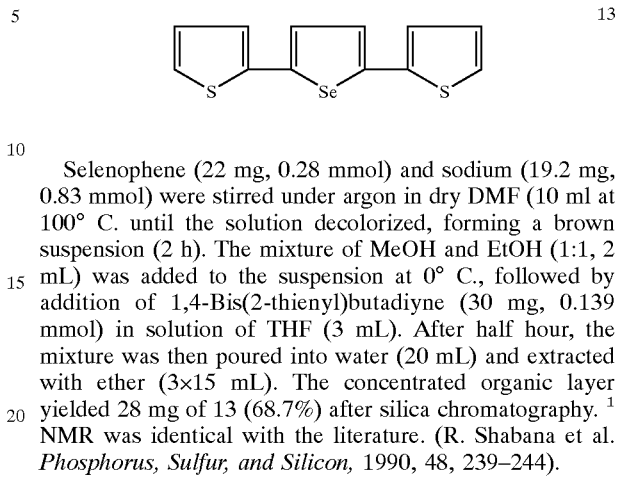

Selenophene (22 mg, 0.28 mmol) and sodium (19.2 mg, 0.83 mmol) were stirred under argon in dry DMF (10 ml at 100° C. until the solution decolorized, forming a brown suspension (2 h). The mixture of MeOH and EtOH (1:1, 2 mL) was added to the suspension at 0° C., followed by addition of 1,4-Bis(2-thienyl)butadiyne (30 mg, 0.139 mmol) in solution of THF (3 mL). After half hour, the mixture was then poured into water (20 mL) and extracted with ether (3×15 mL). The concentrated organic layer yielded 28 mg of 13 (68.7%) after silica chromatography. $^1$NMR was identical with the literature. (R. Shabana et al. *Phosphorus, Sulfur, and Silicon*, 1990, 48, 239–244).

EXAMPLE 46

Preparation of 2,5-Bis-(2'-furyl)selenophene (14)

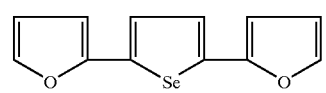

Selenophene (868 mg 11 mmol) and sodium (757 mg, 33 mmol) were stirred under argon in dry DMF (15 mL) at 100° C. until the solution decolorized, forming a brown suspension (2 h). The mixture of MeOH and EtOH (1:1, 3 mL) was added to the suspension at 0° C., followed by addition of 1,4-Bis-(2'-furyl)butadiyne (1 g, 5.5 mmol) in solution of THF (3 mL). After half hour, the mixture was poured into water (20 mL) and extracted with ether (3×20 mL). The concentrated organic layer yielded 0.343 g (24%) of 14 after silica chromatography with hexane as eluent. $^1$H NMR was identical with the literature.(R. Shabana et al. *Phosphorus, Sulfur, and Silicon*, 1990, 48, 239–244).

EXAMPLE 47

Preparation of 5'-Formyl-2,5-bis-(2'-furyl)selenophene (15)

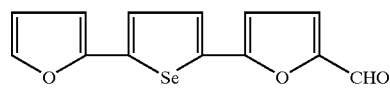

To a solution of 2,5-bis-(2'-furyl)selenophene 14 (0.12 g, 0.456 mmol) in THF, lithium diisopropyl amide (0.73 mmol) was added at −78° C. under argon. The mixture was stirred below −20° C. for 3 h. A large excess of DMF (6.5 mmol) was added at −78° C., and the mixture was allowed to gradually rise to room temperature. Ether (10 mL) was added, and the organic solution was washed with water, dried over sodium sulfate, and evaporated. The crude solid was purified by flash column chromatography over silica gel (ether/hexane) to give monosubstituted aldehydes 15. Yield: 78 mg (60%), which was recrystallized from THF/Hexane to provide pure product. mp: 87.5–89.2° C. $^1$H NMR (CDCl$_3$) δ9.58 (s, 1H), 7.58 (d, 1H, J=4.04), 7.43 (s, 1H), 7.35 (d, 1H, J=4.04), 7.26 (d, 1H, J=3.69), 6.64 (d, 1H, J=3.69), 6.57 (d, 1H, J=3.16), 6.46 (m, 1H).

EXAMPLE 48

Preparation of 5'-Hydroxymethyl-2,5-bis-(2'-furyl) selenophene (16)

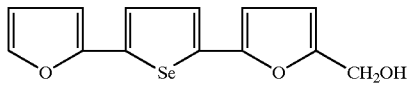

To a solution of 5'-formyl-2,5-bis-(2'-furyl)selenophene (15 mg, 0.05 mmol) in 5 ml THF/MeOH (1:1), excess NaBH$_4$ was added at room temperature. The solution was stirred for 2 h. Ethyl acetate was added, and the organic solution was washed with water, dried over sodium sulfate, and evaporated. The crude solid was purified by recrystallization from THF/Hexane to provide pure product 16. Yield: 14 mg (93.4%). mp: 75.0–77.4° C. $^1$H NMR (CDCl$_3$) δ0.39 (in, 1H), 7.31 (in, 2H), 6.48 (in, 1H), 6.43 (in, 2H), 6.33 (in, 1H). $^{13}$C NMR (THF-d$_8$) δ153.36 (weak), 150.99 (weak), 141.81, 136.66 (weak), 136.19 (weak), 125.46 (weak), 124.99, 124.71, 111.99, 105.89, 105.15, 57.43.

EXAMPLE 49

Preparation of 5',5"-Diformyl-2-(2'-selenyl)-5-2"-thienyl)-thiophene (17)

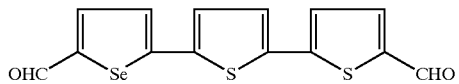

To a solution of 2-(2'-selenyl)-5-(2"-thienyl)thiophene 4 (0.45 g, 1.53 mmol) in THF was added lithium diisopropyl amide (2.44 mmol) at −78° C. under argon. The mixture was stirred below −20° C. for 3 h. Large excess of DMF (13 mmol) was added at −78° C., and the mixture was allowed to gradually rise to room temperature. Ether (30 mL) was added, and the organic solution was washed with water, dried over sodium sulfate, and evaporated. The crude solid was purified by flash column chromatography over silica gel (ether/hexane) to give disubstituted aldehydes 17. Yield: 135 mg (27.3%), which was recrystallized from THF/Hexane to provide pure product. mp: 197.8–199.0° C. $^1$H NNIR (CDCl$_3$) δ9.88 (s, 1H), 9.75 (s, 1H), 7.92 (d, III, J=4.28), 7.69 (d, 1H, J=3.87), 7.46 (d, 1H, J=4.28), 7.30 (d, 1H, J=1.93), 7.29 (d, 1H, J=1.93), 7.26 (d, III, J=3.87).

EXAMPLE 50

Preparation of 5',5"-Dihydroxymethyl-2-(2'-selenyl)-5-(2"-thienyl)-thiophene (18)

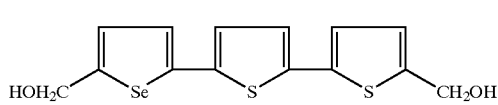

To a solution of 5',5"-diformyl-2-(2'-selenyl)-5-(2"-thienyl)thiophene (12 mg, 0.03 mmol) in 1.5 ml THF/MeOH (1:1), excessive NaBH$_4$ was added at room temperature. The solution was stirred for 4 h. Ethyl acetate was added, and the organic solution was washed with water, dried over sodium sulfate, and evaporated. The crude solid was purified by recrystallization from THF/Hexane to provide pure product 18. Yield: 8.2 mg (68.3%). mp: 187.1–188.8° C. $^1$H NNM (CDCl$_3$) δ7.20 (d, 1H, J=3.76), 7.07 (m, 3H), 7.00 (d, 1H, J=3.66), 6.88 (d, 1H, J=3.39), 5.56 (t, 1H, OH), 5.45 (t, 1H, OH), 4.65 (m, 4H, 2CH$_2$).

EXAMPLE 51

Synthesis of Water Soluble Analogs

A highly polar functional group can be incorporated into the selenophene compounds in order to improve their water solubility. Addition of a carbonylic functional group through an ester linkage (Scheme 5) resulted in a transient solubility. However, the benzylic ester may be readily hydrolyzed to regenerate the water insoluble starting material.

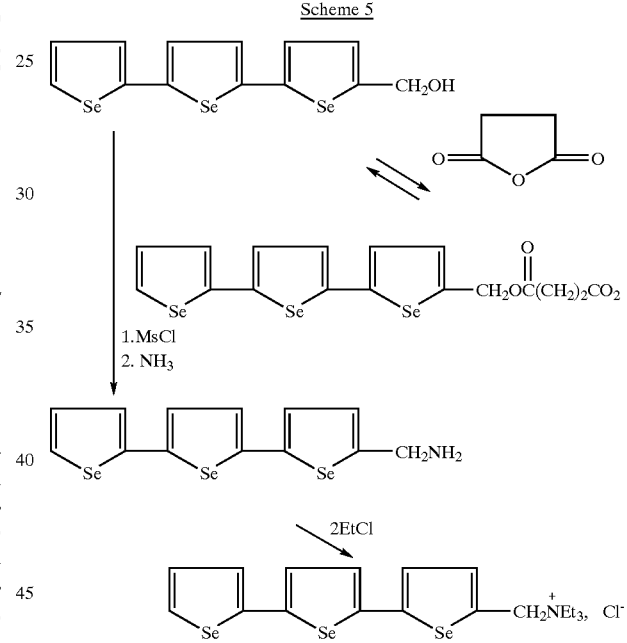

Scheme 5

On the basis of the synthesis for hybrid α-terselenophenes (Scheme 3), a nitrogen atom can be introduced into the five-membered ring system (Scheme 6). Conversion of the hydroxyl group of the intermediate compound of scheme 3 into an amino group can improve water solubility. Further modification of its formulation may further enhance solubility to >1 mg/ml H$_2$O; The ammonium analog should be highly water soluble.

Scheme 6

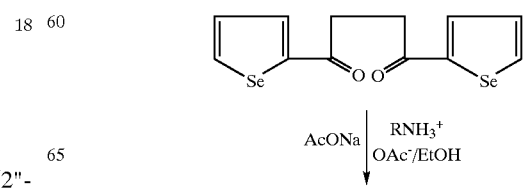

-continued

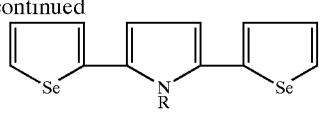

To maximize the efficiency of synthesizing hybrid α-terselenophenes, Scheme 1 can be modified to produce related selenophene analogs in accordance with Scheme 7:

Scheme 7

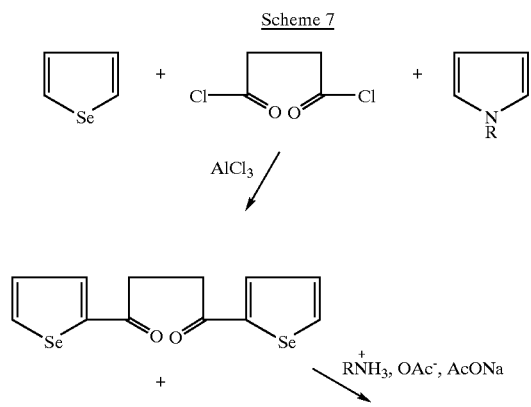

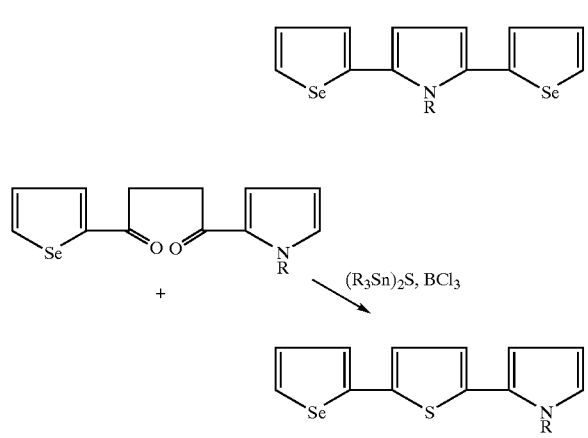

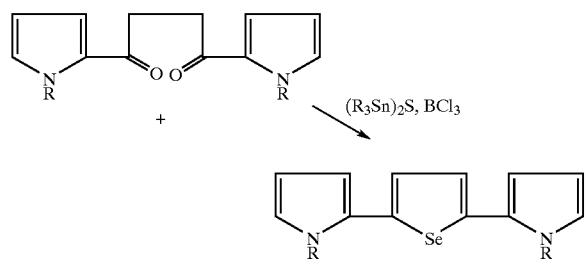

EXAMPLE 52
Synthesis of Prodrugs

An alternative approach of enhancing the water solubility of hydrophobic drugs comprises the preparation of their polar prodrug analogs.

a. Glycosides: Preliminary results indicate that β-D-glucoside of 2-hydroxymethyl-α-terthiophene retains both its in vitro and in vivo activities. Scheme 8 illustrates a procedure utilized for the synthesis of glucoside, galactoside or, glucuronic acid analogs of α-terselenophene:

Scheme 8

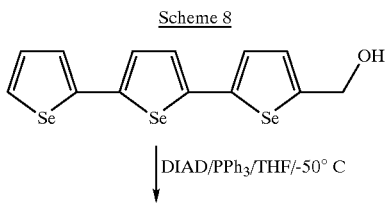

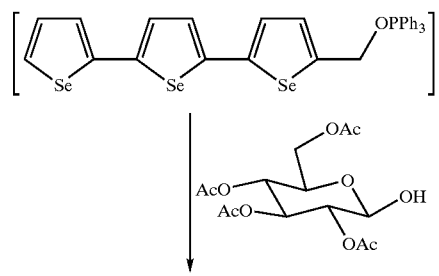

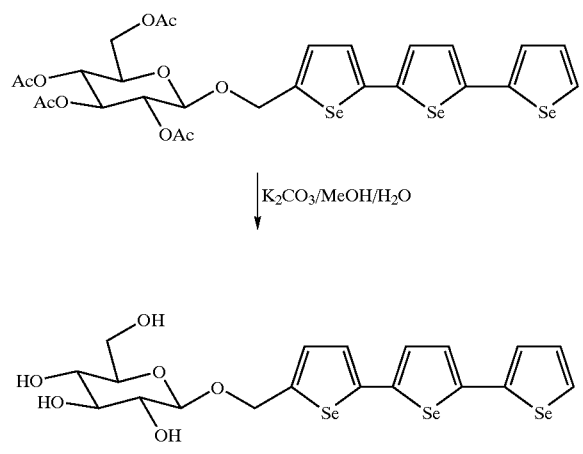

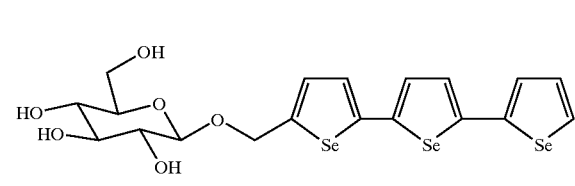

DIAD = diisopropylazodicarboxylate
PPh$_3$ = triphenylphosphine
THF = tetrahydrofuran
K$_2$CO$_3$ = potassium carbonate
MeOH = methanol b. Glutamate Conjugate: As mentioned above, conversion of the hydroxyl group of 2-hydroxymethyl-5,2':5',2''-terselenophene into its amino analog can moderately improve its water solubility. However, the amino analog is less stable. The amino analog may be transformed into its γ-glutamate prodrug (as shown in Scheme 9) to further enhance its water solubility and stability. This conjugate may also enhance target selectivity for the treatment of kidney cancer because of the higher γ-glutamyl transpeptidase activity in kidney. A modified procedure can also be designed for the preparation of glutathione conjugate.

Scheme 9
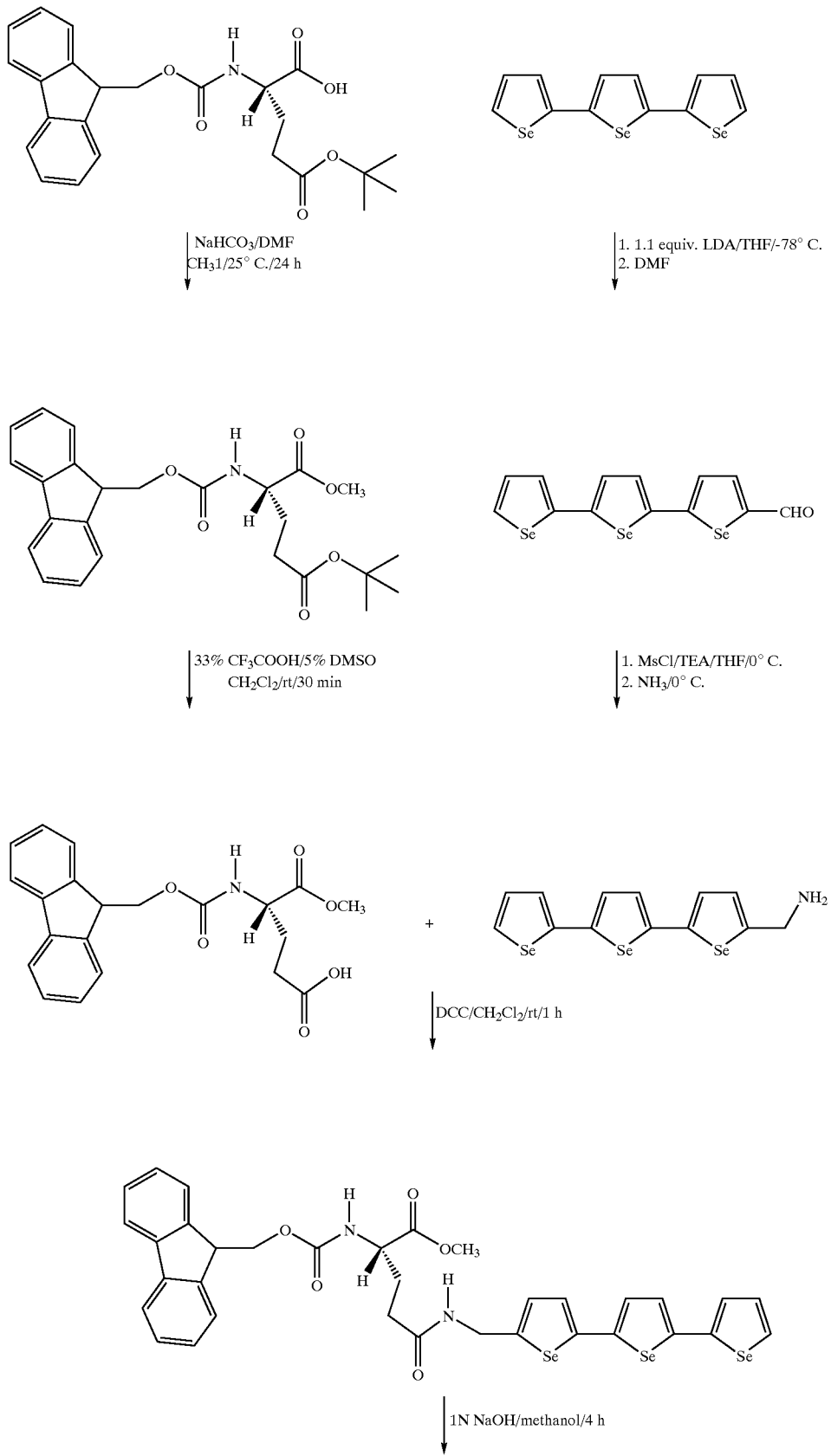

-continued

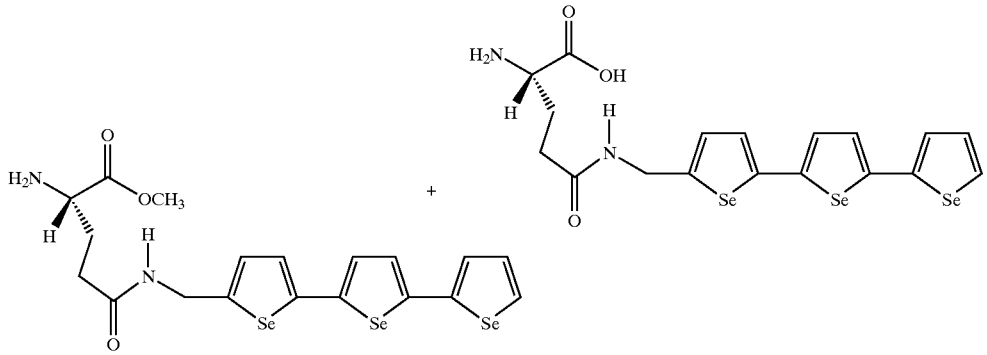

DMF = N,N-dimethylformamide
THF = tetrahydrofuran
DCC = 1,3-dicyclohexylcarbodiimide c. Formation of Inclusion Complexes

The hydrophobic cavity of cyclodextrin derivatives can form stable inclusion complexes with 2-aminomethyl substituted thiophene compounds. β-Cyclodextrin (cyclic heptaamylose) derivatives are commonly used for improving water solubility because of their low costs. It is anticipated that the selenophene compounds of the present invention can be complexed with β-hydroxypropyl) dimethyl and sulfated β-cyclodextrins to enhance the water solubility of those compounds.

EXAMPLE 53

Additional National Cancer Institute data demonstrating selenophene growth inhibition of human cancer cell lines is represented in the following tables. The compound must exhibit a $Log_{10}$ GI50 value of <−4.00 to be considered active against the tested cell line.

NSC: 688829

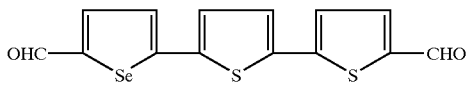

| Panel/Cell Line | $Log_{10}$ GI50 | $Log_{10}$ TGI | $Log_{10}$ LC50 |
|---|---|---|---|
| Leukemia | | | |
| CCRF-CEM | −5.10 | >−4.00 | >−4.00 |
| K-562 | −6.60 | >−4.00 | >−4.00 |
| MOLT-4 | −4.24 | >−4.00 | >−4.00 |
| RPMI-8226 | −4.41 | >−4.00 | >−4.00 |
| SR | −4.61 | −4.14 | >−4.00 |
| Non-Small Cell Lung Cancer | | | |
| A549/ATCC | | >−4.00 | >−4.00 |
| EKVX | >−4.00 | >−4.00 | >−4.00 |
| HOP-62 | −6.60 | −4.80 | >−4.00 |
| HOP-92 | −4.01 | >−4.00 | >−4.00 |
| NCI-H226 | −6.05 | >−4.00 | >−4.00 |
| NCI-H23 | >−4.00 | >−4.00 | >−4.00 |
| NCI-H322M | −4.56 | −4.05 | >−4.00 |
| NCI-H460 | −6.85 | >−4.00 | >−4.00 |
| NCI-H522 | −4.95 | −4.40 | >−4.00 |
| Colon Cancer | | | |
| COLO 205 | −4.92 | −4.48 | −4.04 |
| HCC-2998 | −6.41 | >−4.00 | >−4.00 |
| HCT-116 | −6.53 | >−4.00 | >−4.00 |

-continued

NSC: 688829

| Panel/Cell Line | $Log_{10}$ GI50 | $Log_{10}$ TGI | $Log_{10}$ LC50 |
|---|---|---|---|
| HCT-15 | −4.64 | >−4.00 | >−4.00 |
| HT29 | −4.63 | >−4.00 | >−4.00 |
| KM12 | | >−4.00 | >−4.00 |
| SW-620 | −6.08 | >−4.00 | >−4.00 |
| CNS Cancer | | | |
| SF-295 | >−4.00 | >−4.00 | >−4.00 |
| SF-539 | −4.56 | >−4.00 | >−4.00 |
| SNB-19 | >−4.00 | >−4.00 | >−4.00 |
| SNB-75 | −4.12 | >−4.00 | >−4.00 |
| U251 | −6.61 | −4.59 | >−4.00 |
| Melanoma | | | |
| LOX IMVI | −4.78 | >−4.00 | >−4.00 |
| MALME-3M | −4.54 | >−4.00 | >−4.00 |
| M14 | −4.70 | >−4.00 | >−4.00 |
| SK-MEL-2 | −4.47 | >−4.00 | >−4.00 |
| SK-MEL-28 | −4.18 | >−4.00 | >−4.00 |
| SK-MEL-5 | −4.63 | >−4.00 | >−4.00 |
| UACC-257 | −6.71 | −6.29 | >−4.00 |
| UACC-62 | −6.85 | >−4.00 | >−4.00 |
| Ovarian Cancer | | | |
| IGROV1 | −6.75 | −5.61 | −4.04 |
| OVCAR-3 | −6.89 | −6.20 | >−4.00 |
| OVCAR-4 | −6.73 | | >−4.00 |
| OVCAR-5 | −6.91 | −6.30 | >−4.00 |
| OVCAR-8 | −4.82 | −4.03 | >−4.00 |
| SK-OV-3 | −4.58 | >−4.00 | >−4.00 |
| Renal Cancer | | | |
| 786-0 | | −4.57 | −4.19 |
| A498 | −7.67 | −7.10 | −6.48 |
| ACHN | >−4.00 | >−4.00 | >−4.00 |
| CAKI-1 | −6.72 | −6.30 | −4.53 |
| SN12C | −4.55 | −4.07 | >−4.00 |
| TK-10 | −7.55 | −6.68 | −4.21 |
| UO-31 | >−4.00 | >−4.00 | >−4.00 |
| Prostate Cancer | | | |
| PC-3 | −4.55 | >−4.00 | >−4.00 |
| DU-145 | >−4.00 | >−4.00 | >−4.00 |
| Breast Cancer | | | |
| MCF7 | −6.72 | >−4.00 | >−4.00 |
| MCF7/ADR-RES | −4.52 | >−4.00 | >−4.00 |

-continued

NSC: 688829

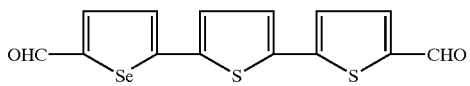

| Panel/Cell Line | Log$_{10}$ GI50 | Log$_{10}$ TGI | Log$_{10}$ LC50 |
|---|---|---|---|
| MDA-MB-231/ATCC | −4.63 | −4.17 | >−4.00 |
| HS 578T | −5.54 | >−4.00 | >−4.00 |
| MDA-MB-435 | −4.48 | >−4.00 | >−4.00 |
| MDA-N | −4.68 | >−4.00 | >−4.00 |
| BT-549 | −4.25 | >−4.00 | >−4.00 |
| T-47D | −6.47 | >−4.00 | >−4.00 |
| MG_MID | −5.27 | −4.35 | −4.06 |
| Delta | 2.40 | 2.75 | 2.42 |
| Range | 3.67 | 3.10 | 2.48 |

NSC: 688830

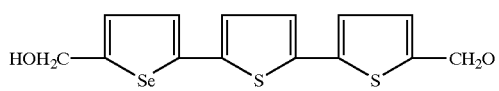

| Panel/Cell Line | Log$_{10}$ GI50 | Log$_{10}$ TGI | Log$_{10}$ LC50 |
|---|---|---|---|
| Leukemia | | | |
| CCRF-CEM | −4.59 | >−4.00 | >−4.00 |
| K-562 | −7.14 | −4.76 | −4.01 |
| MOLT-4 | −4.41 | >−4.00 | >−4.00 |
| RPMI-8226 | −4.43 | >−4.00 | >−4.00 |
| SR | −4.61 | −4.14 | >−4.00 |
| Non-Small Cell Lung Cancer | | | |
| A549/ATCC | −5.22 | −4.48 | >−4.00 |
| EKVX | −4.71 | −4.18 | >−4.00 |
| HOP-62 | −7.21 | −4.55 | −4.07 |
| HOP-92 | −4.55 | >−4.00 | >−4.00 |
| NCI-H322M | −7.22 | | |
| NCI-H23 | −4.07 | >−4.00 | >−4.00 |
| NCI-H322M | −5.47 | −4.70 | >−4.00 |
| NCI-H460 | −7.77 | −6.19 | −4.54 |
| NCI-H522 | >−4.00 | >−4.00 | >−4.00 |
| Colon Cancer | | | |
| COLO 205 | −6.35 | −5.26 | −4.21 |
| HCC-2998 | −7.20 | −4.94 | −4.35 |
| HCT-116 | −7.56 | −4.76 | −4.09 |
| HCT-15 | −4.54 | >−4.00 | >−4.00 |
| HT29 | −6.65 | −4.36 | >−4.00 |
| KM12 | −4.32 | >−4.00 | >−4.00 |
| SW-620 | −7.40 | −4.60 | |
| CNS Cancer | | | |
| SF-295 | −4.68 | −4.25 | >−4.00 |
| SF-539 | −4.81 | −4.44 | −4.08 |
| SNB-19 | −4.47 | −4.06 | >−4.00 |
| SNB-75 | −4.59 | >−4.00 | >−4.00 |
| U251 | −7.08 | −4.68 | −4.14 |
| Melanoma | | | |
| LOXIMVI | −4.87 | 4.56 | 4.25 |
| MALME-3M | −4.36 | >−4.00 | >−4.00 |
| M14 | −4.43 | >−4.00 | >−4.00 |
| SK-MEL-2 | −4.40 | >−4.00 | >−4.00 |
| SK-MEL-28 | >−4.00 | >−4.00 | >−4.00 |
| SK-MEL-5 | −4.44 | >−4.00 | >−4.00 |
| UACC-257 | −7.78 | −7.34 | −6.62 |
| UACC-62 | −7.87 | >−4.00 | >−4.00 |

-continued

NSC: 688830

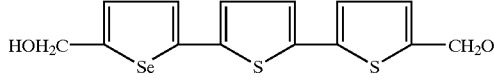

| Panel/Cell Line | Log$_{10}$ GI50 | Log$_{10}$ TGI | Log$_{10}$ LC50 |
|---|---|---|---|
| Ovarian Cancer | | | |
| IGROVI | −7.85 | −6.76 | −4.55 |
| OVCAR-3 | <−8.00 | −7.25 | −4.30 |
| OVCAR-4 | −6.98 | | −4.09 |
| OVCAR-5 | −7.64 | | >−4.00 |
| OVCAR-8 | −5.16 | −4.51 | >−4.00 |
| SK-OV-3 | −5.49 | −4.71 | −4.29 |
| Renal Cancer | | | |
| 786-0 | −5.19 | −4.64 | −4.24 |
| A498 | <−8.00 | −7.61 | −7.14 |
| ACHN | −4.68 | >−4.00 | >−4.00 |
| CAKI-1 | <−8.00 | −7.55 | |
| SN12C | −4.31 | >−4.00 | >−4.00 |
| TK-10 | <−8.00 | −7.43 | −4.19 |
| UO-31 | >−4.00 | >−4.00 | >−4.00 |
| Prostate Cancer | | | |
| PC-3 | −4.51 | >−4.00 | >−4.00 |
| DU-145 | −4.64 | >−4.00 | >−4.00 |
| Breast Cancer | | | |
| MCF7 | −7.78 | >−4.00 | >−4.00 |
| MCF7/ADR-RES | −4.91 | >−4.00 | >−4.00 |
| MDA-MB-231/ATCC | −4.90 | −4.45 | −4.01 |
| HS 578T | | >−4.00 | >−4.00 |
| MDA-MB-435 | >−4.00 | >−4.00 | >−4.00 |
| MDA-N | −4.01 | >−4.00 | >−4.00 |
| BT-549 | >−4.00 | >−4.00 | >−4.00 |
| T-47D | −6.54 | −4.24 | |
| MG_MID | −5.64 | −4.62 | −4.16 |
| Delta | 2.36 | 2.99 | 2.98 |
| Range | 4.00 | 3.61 | 3.14 |

NSC: 676631

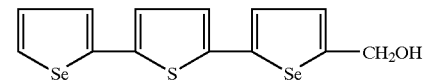

| Panel/Cell Line | Log$_{10}$ GI50 | Log$_{10}$ TGI | Log$_{10}$ LC50 |
|---|---|---|---|
| Leukemia | | | |
| CCRF-CEM | >−4.00 | >−4.00 | >−4.00 |
| HL-60(TB) | >−4.00 | >−4.00 | >−4.00 |
| K-562 | −6.99 | >−4.00 | >−4.00 |
| MOLT-4 | >−4.00 | >−4.00 | >−4.00 |
| RPMI-8226 | >−4.00 | >−4.00 | >−4.00 |
| SR | >−4.00 | >−4.00 | >−4.00 |
| Non-Small Cell Lung Cancer | | | |
| A549/ATCC | −4.23 | >−4.00 | >−4.00 |
| EKVX | >−4.00 | >−4.00 | >−4.00 |
| HOP-62 | | >−4.00 | >−4.00 |
| HOP-92 | >−4.00 | >−4.00 | >−4.00 |
| NCI-H226 | −7.30 | −6.74 | −6.28 |
| NCI-H23 | −4.78 | −4.41 | −4.04 |
| NCI-H322M | −4.66 | >−4.00 | >−4.00 |
| NCI-H460 | | >−4.00 | >−4.00 |
| NCI-H522 | −5.28 | −4.67 | −4.26 |

-continued

NSC: 676631

[Structure: Se-S-Se-CH₂OH terthiophene-like]

| Panel/Cell Line | Log₁₀ GI50 | Log₁₀ TGI | Log₁₀ LC50 |
|---|---|---|---|
| Colon Cancer | | | |
| COLO 205 | −6.54 | −4.90 | −4.18 |
| HCC-2998 | −4.37 | >−4.00 | >−4.00 |
| HCT-116 | −7.27 | >−4.00 | >−4.00 |
| HCT-15 | −4.56 | >−4.00 | >−4.00 |
| HT29 | | >−4.00 | >−4.00 |
| KM12 | −4.57 | >−4.00 | >−4.00 |
| SW-620 | −6.45 | >−4.00 | >−4.00 |
| CNS Cancer | | | |
| SF-268 | −4.63 | −4.19 | >−4.00 |
| SF-295 | −4.26 | >−4.00 | >−4.00 |
| SF-539 | −4.91 | −4.24 | >−4.00 |
| SNB-19 | −4.76 | >−4.00 | >−4.00 |
| SNB-75 | −4.38 | >−4.00 | >−4.00 |
| U251 | −7.11 | −4.70 | −4.35 |
| Melanoma | | | |
| LOX IMVI | −4.82 | −4.44 | −4.07 |
| MALME-3M | >−4.00 | >−4.00 | >−4.00 |
| M14 | −4.70 | >−4.00 | >−4.00 |
| SK-MEL-2 | >−4.00 | >−4.00 | >−4.00 |
| SK-MEL-28 | −4.18 | >−4.00 | >−4.00 |
| SK-MEL-5 | >−4.00 | >−4.00 | >−4.00 |
| UACC-257 | −7.50 | >−4.00 | −6.34 |
| UACC-62 | −7.58 | −6.94 | >−4.00 |
| Ovarian Cancer | | | |
| IGROV1 | −7.09 | −6.22 | −4.29 |
| OVCAR-3 | −7.56 | −6.86 | −4.39 |
| OVCAR-4 | | >−4.00 | >−4.00 |
| OVCAR-5 | −7.50 | −6.68 | |
| OVCAR-8 | −4.61 | >−4.00 | >−4.00 |
| SK-OV-3 | −4.34 | >−4.00 | >−4.00 |
| Renal Cancer | | | |
| 786-0 | >−4.00 | >−4.00 | >−4.00 |
| A498 | −7.56 | −7.08 | −6.52 |
| ACHN | >4.00 | >−4.00 | >−4.00 |
| CAKI-1 | −7.51 | −6.72 | −4.19 |
| RXF-393 | −4.14 | >−4.00 | >−4.00 |
| SN12C | >−4.00 | >−4.00 | >−4.00 |
| TK-10 | −7.30 | −6.43 | −4.14 |
| UO-31 | >−4.00 | >−4.00 | >−4.00 |
| Prostate Cancer | | | |
| PC-3 | −4.28 | >−4.00 | >−4.00 |
| DU-145 | −4.70 | −4.11 | >−4.00 |
| Breast Cancer | | | |
| MCF7 | −7.03 | −4.66 | >−4.00 |
| MCF7/ADR-RES | −5.00 | −4.50 | −4.01 |
| MDA-MB-231/ATCC | −4.72 | −4.06 | >−4.00 |
| HS 578T | >−4.00 | >−4.00 | >−4.00 |
| MDA-MB-435 | −5.09 | −4.26 | >−4.00 |
| MBA-N | −4.78 | −4.36 | >−4.00 |
| BT-549 | −4.77 | −4.42 | −4.06 |
| T-47D | −6.17 | >−4.00 | >−4.00 |
| MG_MID | −5.18 | −4.47 | −4.15 |
| Delta | 2.40 | 2.61 | 2.37 |
| Range | 3.58 | 3.08 | 2.52 |

NSC: 675246

[Structure: Se-Se-Se-CH₂OH triselenophene]

| Panel/Cell Line | Log₁₀ GI50 | Log₁₀ TGI | Log₁₀ LC50 |
|---|---|---|---|
| Leukemia | | | |
| CCRF-CEM | −5.50 | −4.91 | >−4.00 |
| HL-60(TB) | −5.24 | >−4.00 | >−4.00 |
| K-562 | −6.43 | −5.12 | >−4.00 |
| MOLT-4 | −5.49 | −4.92 | >−4.00 |
| RPMI-8226 | −5.13 | >−4.00 | >−4.00 |
| SR | −5.18 | >−4.00 | >−4.00 |
| Non-Small Cell Lung Cancer | | | |
| A549/ATCC | −4.98 | −4.65 | −4.33 |
| EKVX | −5.26 | −4.76 | −4.37 |
| HOP-62 | −5.14 | −4.69 | −4.35 |
| HOP-92 | −5.58 | −4.95 | −4.42 |
| NCI-H322M | −6.21 | −5.63 | |
| NCI-H23 | −4.88 | −4.51 | −4.15 |
| NCI-H322M | −4.97 | −4.65 | −4.32 |
| NCI-H460 | −6.49 | −5.44 | −4.64 |
| NCI-H52 | −5.61 | −5.18 | −4.63 |
| Colon Cancer | | | |
| COLO 205 | −6.00 | −5.39 | >−4.00 |
| HCC-2998 | −5.91 | −4.93 | −4.27 |
| HCT-116 | −7.19 | −4.97 | −4.49 |
| HCT-15 | −5.37 | −4.75 | >−4.00 |
| HT29 | −6.07 | −4.97 | −4.23 |
| KM12 | −5.38 | −4.77 | −4.28 |
| SW-620 | −6.38 | −4.99 | −4.45 |
| CNS Cancer | | | |
| SF-268 | −5.39 | >−4.00 | >−4.00 |
| SF-295 | −4.97 | −4.56 | −4.14 |
| SF-539 | −4.91 | −4.60 | −4.29 |
| SNB-19 | −4.91 | −4.28 | >−4.00 |
| SNB-75 | −5.41 | >−4.00 | >−4.00 |
| U251 | −7.15 | −4.91 | −4.26 |
| Melanoma | | | |
| LOXIMVI | −5.44 | −5.01 | −4.43 |
| MALME-3M | −5.21 | −4.71 | −4.30 |
| M14 | −5.06 | −4.62 | −4.21 |
| SK-MEL-2 | −5.04 | −4.59 | −4.16 |
| SK-MEL-28 | −5.13 | −4.66 | −4.27 |
| SK-MEL-5 | −5.58 | −5.05 | −4.53 |
| UACC-257 | −7.30 | −6.65 | |
| UACC-62 | −7.99 | −4.95 | −4.17 |
| Ovarian Cancer | | | |
| IGROV1 | −7.27 | −5.65 | −4.91 |
| OVCAR-3 | −7.22 | −5.89 | −5.16 |
| OVCAR-4 | −6.24 | −4.91 | −4.32 |
| OVCAR-5 | −6.74 | −4.60 | >−4.00 |
| OVCAR-8 | −5.30 | −4.48 | >−4.00 |
| Renal Cancer | | | |
| 786-0 | −5.66 | −5.28 | −4.76 |
| A498 | −7.41 | −6.78 | −6.16 |
| CAKI-1 | −5.27 | −4.73 | −4.29 |
| RXF-393 | −7.68 | −7.04 | |
| TK-10 | −5.72 | −4.97 | >−4.00 |
| UO-31 | −5.21 | −4.41 | >−4.00 |
| | −7.50 | −6.65 | −4.05 |
| | −4.92 | −4.61 | −4.29 |
| Prostate Cancer | | | |
| PC-3 | −5.42 | −4.88 | −4.44 |
| DU-145 | −4.99 | −4.66 | −4.33 |

-continued

NSC: 675246

[Structure: three selenophene rings with CH₂OH substituent]

| Panel/Cell Line | Log₁₀ GI50 | Log₁₀ TGI | Log₁₀ LC50 |
| --- | --- | --- | --- |
| Breast Cancer | | | |
| MCF7 | −6.84 | −5.42 | −4.53 |
| MCF7/ADR-RES | −5.29 | −4.33 | >−4.00 |
| MDA-MB-231/ATCC | −5.36 | −4.47 | >−4.00 |
| MDA-N | −5.01 | −4.25 | >−4.00 |
| T-47D | −5.42 | −4.82 | −4.35 |
| | −5.56 | −4.90 | −4.40 |
| | −5.20 | −4.68 | −4.26 |
| | −5.63 | −4.33 | >−4.00 |
| MG_MID | −5.78 | −4.91 | −4.29 |
| Delta | 2.22 | 2.14 | 1.88 |
| Range | 3.11 | 3.04 | 2.16 |

NSC: 675247

[Structure: OH₂C—three selenophene rings—CH₂OH]

| Panel/Cell Line | Log₁₀ GI50 | Log₁₀ TGI | Log₁₀ LC50 |
| --- | --- | --- | --- |
| Leukemia | | | |
| CCRF-CEM | −5.47 | −5.00 | >−4.00 |
| HL-60(TB) | −5.39 | | |
| K-562 | −5.88 | −5.30 | −4.15 |
| MOLT-4 | −5.48 | −5.08 | >−4.00 |
| RPMI-8226 | −5.39 | >−4.00 | >−4.00 |
| SR | −5.43 | >−4.00 | >−4.00 |
| | | | >−4.00 |
| Non-Small Cell Lung Cancer | | | |
| A549/ATCC | −5.34 | −4.71 | −4.27 |
| EKVX | −5.30 | −4.46 | >−4.00 |
| HOP-62 | −5.26 | −4.67 | −4.24 |
| HOP-92 | −5.62 | −5.12 | −4.26 |
| NCI-H226 | −5.77 | −5.41 | −5.04 |
| NCI-H23 | −5.18 | −4.60 | −4.02 |
| NCI-H322M | −4.95 | −4.61 | −4.28 |
| NCI-H460 | −6.28 | −5.00 | −4.09 |
| NCI-H522 | −5.78 | −5.47 | −5.15 |
| Colon Cancer | | | |
| COLO 205 | −5.71 | −5.29 | −4.75 |
| HCC-2998 | −6.07 | −5.49 | −4.90 |
| HCT-116 | −6.27 | −4.95 | >−4.00 |
| HCT-15 | −5.42 | −4.91 | −4.26 |
| HT29 | −5.79 | −5.12 | −4.18 |
| KM12 | −5.35 | −4.82 | −4.30 |
| SW-620 | −5.87 | −5.44 | −5.02 |
| CNS Cancer | | | |
| SF-268 | −5.76 | −5.36 | 4.68 |
| SF-295 | −4.93 | −4.54 | −4.15 |
| SF-539 | −4.76 | −4.39 | −4.02 |
| SNB-19 | −5.26 | −4.60 | −4.04 |
| SNB-75 | −4.83 | −4.41 | >−4.00 |
| U251 | −6.33 | −4.91 | −4.30 |
| Melanoma | | | |
| LOX IMVI | −5.52 | −5.15 | >−4.00 |
| MALME-3M | −5.54 | −4.97 | −4.25 |
| M14 | −5.43 | −4.89 | −4.31 |
| SK-MEL-2 | −5.15 | −4.62 | −4.16 |

-continued

NSC: 675247

[Structure: OH₂C—three selenophene rings—CH₂OH]

| Panel/Cell Line | Log₁₀ GI50 | Log₁₀ TGI | Log₁₀ LC50 |
| --- | --- | --- | --- |
| SK-MEL-28 | −5.29 | >−4.00 | >−4.00 |
| SK-MEL-5 | −5.84 | −5.52 | −5.20 |
| UACC-257 | −6.36 | −5.70 | −4.50 |
| UACC-62 | −6.81 | −5.61 | −4.35 |
| Ovarian Cancer | | | |
| IGROV1 | −5.86 | −5.19 | −4.52 |
| OVCAR-3 | −6.68 | −5.93 | −5.27 |
| OVCAR-4 | −5.77 | −5.16 | −4.31 |
| OVCAR-5 | −5.88 | −4.89 | >−4.00 |
| OVCAR-8 | −5.43 | −4.75 | −4.14 |
| Renal Cancer | | | |
| 786-0 | −5.56 | −5.20 | −4.15 |
| A498 | −6.42 | −5.85 | −5.14 |
| ACHN | −5.40 | >−4.00 | >−4.00 |
| CAKI-1 | −7.13 | −6.33 | −4.88 |
| RXF-393 | −5.80 | −5.43 | −5.06 |
| SN12C | −5.56 | −4.93 | >−4.00 |
| TK-10 | −6.86 | −6.18 | −4.80 |
| UO-31 | −5.28 | −4.83 | −4.41 |
| Prostate Cancer | | | |
| PC-3 | −5.45 | −4.91 | −4.45 |
| DU-145 | −5.16 | −4.71 | −4.33 |
| Breast Cancer | | | |
| MCF7 | −6.80 | −4.95 | −4.32 |
| MCF7/ADR-RES | −5.42 | −4.58 | >−4.00 |
| MDA-MB-3221/ATCC | −5.30 | −4.79 | −4.32 |
| | −5.27 | −4.44 | >−4.00 |
| HS 578T | −5.49 | −4.95 | −4.33 |
| MDA-MB-435 | −5.53 | −5.01 | −4.31 |
| MDA-N | −5.11 | −4.60 | −4.13 |
| BT-549 | −5.47 | −4.85 | >−4.00 |
| T-47D | | | |
| MG_MID | −5.65 | −4.98 | −4.34 |
| Delta | 1.48 | 1.36 | 0.93 |
| Range | 2.37 | 2.33 | 1.27 |

NSC: 675343

[Structure: HOH₂C—thiophene—selenophene—thiophene—CH₂OH]

| Panel/Cell Line | Log₁₀ GI50 | Log₁₀ TGI | Log₁₀ LC50 |
| --- | --- | --- | --- |
| Leukemia | | | |
| CCRF-CEM | −4.65 | −4.22 | >−4.00 |
| HL-60(TB) | −4.21 | >−4.00 | >−4.00 |
| K-562 | <−8.00 | −4.58 | >−4.00 |
| MOLT-4 | −4.54 | −4.06 | >−4.00 |
| RPMI-8226 | >−4.00 | >−4.00 | >−4.00 |
| SR | >−4.00 | >−4.00 | >−4.00 |
| Non-Small Cell Lung Cancer | | | |
| A549/ATCC | >−4.00 | >−4.00 | >−4.00 |
| EKVX | >−4.00 | >−4.00 | >−4.00 |
| HOP-62 | >−4.00 | >−4.00 | >−4.00 |
| HOP-92 | −4.39 | >−4.00 | >−4.00 |
| NCI-H226 | <−8.00 | −7.14 | >−4.00 |
| NCI-H23 | >−4.00 | >−4.00 | >−4.00 |
| NCI-H322M | −5.01 | >−4.00 | >−4.00 |

-continued

NSC: 675343

HOH$_2$C—[thiophene]—[selenophene]—[thiophene]—CH$_2$OH

| Panel/Cell Line | Log$_{10}$ GI50 | Log$_{10}$ TGI | Log$_{10}$ LC50 |
|---|---|---|---|
| NCI-H460 | <−8.00 | >−4.00 | >−4.00 |
| NCI-H522 | −4.00 | >−4.00 | >−4.00 |
| Colon Cancer | | | |
| COLO 205 | <−8.00 | −5.98 | −4.64 |
| HCC-2998 | <−8.00 | −5.47 | >−4.00 |
| HCT-116 | <−8.00 | >−4.00 | >−4.00 |
| HCT-15 | >−4.00 | >−4.00 | >−4.00 |
| HT29 | | >−4.00 | >−4.00 |
| KM12 | >−4.00 | >−4.00 | >−4.00 |
| SW-620 | <−8.00 | >−4.00 | >−4.00 |
| CNS Cancer | | | |
| SF-268 | >−4.00 | >−4.00 | >−4.00 |
| SF-295 | >−4.00 | >−4.00 | >−4.00 |
| SF-539 | >−4.00 | >−4.00 | >−4.00 |
| SNB-19 | >−4.00 | >−4.00 | >−4.00 |
| SNB-75 | | | |
| U251 | <−8.00 | >−4.00 | >−4.00 |
| Melanoma | | | |
| LOX IMVI | >−4.00 | >−4.00 | >−4.00 |
| MALME-3M | >−4.00 | >−4.00 | >−4.00 |
| M14 | >−4.00 | >−4.00 | >−4.00 |
| SK-MEL-2 | >−4.00 | >−4.00 | >−4.00 |
| SK-MEL-28 | >−4.00 | >−4.00 | >−4.00 |
| SK-MEL-5 | | >−4.00 | >−4.00 |
| UACC-257 | <−8.00 | <−8.00 | |
| UACC-62 | <−8.00 | >−4.00 | >−4.00 |
| Ovarian Cancer | | | |
| OVCAR-3 | −7.59 | −4.49 | >−4.00 |
| OVCAR-4 | <−8.00 | >−4.00 | >−4.00 |
| OVCAR-5 | −6.80 | >−4.00 | >−4.00 |
| OVCAR-8 | <−8.00 | >−4.00 | >−4.00 |
| SK-OV-3 | >−4.00 | >−4.00 | >−4.00 |
| Renal Cancer | | | |
| 786-0 | >−4.00 | >−4.00 | >−4.00 |
| A498 | <−8.00 | <−8.00 | −6.80 |
| ACHN | >−4.00 | >−4.00 | >−4.00 |
| CAKI-1 | <−8.00 | <−8.00 | >−4.00 |
| RXF-393 | −4.68 | >−4.00 | >−4.00 |
| SN12C | >−4.00 | >−4.00 | >−4.00 |
| TK-10 | <−8.00 | <−8.00 | >−4.00 |
| UO-31 | >−4.00 | >−4.00 | >−4.00 |
| Prostate Cancer | | | |
| PC-3 | >−4.00 | >−4.00 | >−4.00 |
| DU-145 | >−4.00 | >−4.00 | >−4.00 |
| Breast Cancer | | | |
| MCF7 | <−8.00 | >−4.00 | >−4.00 |
| MCF7/ADR-RES | >−4.00 | >−4.00 | >−4.00 |
| MDA-MB-231/ATCC | >−4.00 | >−4.00 | >−4.00 |
| HS 578T | >−4.00 | >−4.00 | >−4.00 |
| MDA-MB-435 | >−4.00 | >−4.00 | >−4.00 |
| MDA-N | >−4.00 | >−4.00 | >−4.00 |
| BT-549 | >−4.00 | >−4.00 | >−4.00 |
| T-47D | −6.14 | >−4.00 | >−4.00 |
| MG_MID | | | |
| Delta | −5.36 | −4.41 | −4.06 |
| Range | 2.64 | 3.59 | 2.74 |
| | 4.00 | 4.00 | 2.80 |

NSC: 676632

HOH$_2$C—[selenophene]—[thiophene]—[selenophene]—CH$_2$OH

| Panel/Cell Line | Log$_{10}$ GI50 | Log$_{10}$ TGI | Log$_{10}$ LC50 |
|---|---|---|---|
| Leukemia | | | |
| CCRF-CEM | −4.06 | >−4.00 | >−4.00 |
| HL-60(TB) | >−4.00 | >−4.00 | >−4.00 |
| K-562 | −7.32 | >−4.00 | >−4.00 |
| MOLT-4 | >−4.00 | >−4.00 | >−4.00 |
| RPM1-8226 | >−4.00 | >−4.00 | >−4.00 |
| SR | >−4.00 | >−4.00 | >−4.00 |
| Non-Small Cell Lung | | | |
| Cancer | −5.58 | >−4.00 | >−4.00 |
| A549/ATCC | −4.30 | >−4.00 | >−4.00 |
| EKVX | −7.12 | >−4.00 | >−4.00 |
| HOP-62 | >−4.00 | >−4.00 | >−4.00 |
| HOP-92 | −7.71 | −7.27 | −6.49 |
| NCI-H226 | >−4.00 | >−4.00 | >−4.00 |
| NCI-H23 | >−4.00 | >−4.00 | >−4.00 |
| NCI-H322M | −7.33 | >−4.00 | >−4.00 |
| NCI-H460 | >−4.00 | >−4.00 | >−4.00 |
| NCI-H522 | | | |
| Colon Cancer | | | |
| HCC-2998 | −6.75 | −6.26 | −5.61 |
| HCT-116 | >−4.00 | >−4.00 | >−4.00 |
| HCT-15 | −7.35 | >−4.00 | >−4.00 |
| HT29 | >−4.00 | >−4.00 | >−4.00 |
| KM12 | −6.27 | >−4.00 | >−4.00 |
| SW-620 | >−4.00 | >−4.00 | >−4.00 |
| | −6.82 | >−4.00 | >−4.00 |
| CNS Cancer | | | |
| SF-268 | >−4.00 | >−4.00 | >−4.00 |
| SF-295 | >−4.00 | >−4.00 | >−4.00 |
| SF-539 | >−4.00 | >−4.00 | >−4.00 |
| SNB-19 | −4.37 | >−4.00 | >−4.00 |
| SNB-75 | >−4.00 | >−4.00 | >−4.00 |
| U251 | −7.45 | −4.92 | −4.33 |
| Melanoma | | | |
| LOX IMVI | >−4.00 | <−4.00 | >−4.00 |
| MALME-3M | >−4.00 | >−4.00 | >−4.00 |
| M14 | >−4.00 | >−4.00 | >−4.00 |
| SK-MEL-2 | >−4.00 | >−4.00 | >−4.00 |
| SK-MEL-28 | >−4.00 | >−4.00 | >−4.00 |
| SK-MEL-5 | −4.20 | >−4.00 | >−4.00 |
| UACC-257 | −7.67 | >−4.00 | |
| UACC-62 | −7.65 | −7.25 | >−4.00 |
| Ovarian Cancer | | | |
| IGROV1 | −7.49 | −6.56 | >−4.00 |
| OVCAR-3 | −7.71 | −7.17 | >−4.00 |
| OVCAR-4 | −6.87 | | >−4.00 |
| OVCAR-5 | −7.88 | −7.11 | −6.11 |
| OVCAR-8 | >−4.00 | >−4.00 | >−4.00 |
| | >−4.00 | >−4.00 | >−4.00 |
| Renal Cancer | | | |
| 786-0 | >−4.00 | >−4.00 | >−4.00 |
| A498 | −7.73 | −7.37 | −7.02 |
| ACHN | >−4.00 | >−4.00 | >−4.00 |
| CAKI-1 | −7.90 | −6.91 | >−4.00 |
| RXF-393 | >−4.00 | >−4.00 | >−4.00 |
| SN12C | >−4.00 | >−4.00 | >−4.00 |
| TK-10 | −7.55 | −7.09 | >−4.00 |
| UO-31 | >−4.00 | >−4.00 | >−4.00 |
| Prostate Cancer | | | |
| PC-3 | >−4.00 | >−4.00 | >−4.00 |
| DU-145 | −4.02 | >−4.00 | >−4.00 |

-continued

NSC: 676632

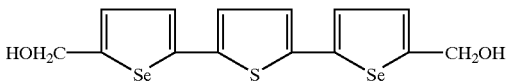

| Panel/Cell Line | Log₁₀ GI50 | Log₁₀ TGI | Log₁₀ LC50 |
|---|---|---|---|
| Breast Cancer | | | |
| MCF7 | −7.91 | >−4.00 | >−4.00 |
| MCF7/ADR-RES | >−4.00 | >−4.00 | >−4.00 |
| MDA-MIB-231/ATCC | >−4.00 | >−4.00 | >−4.00 |
| HS578T | >−4.00 | >−4.00 | >−4.00 |
| MDA-MB-435 | >−4.00 | >−4.00 | >−4.00 |
| MDA-N | >−4.00 | >−4.00 | >−4.00 |
| BT-549 | −6.71 | >−4.00 | >−4.00 |
| T-47D | | | |
| MG_MID | −5.16 | −4.48 | −4.16 |
| Delta | 2.75 | 2.89 | 2.86 |
| Range | 3.91 | 3.37 | 3.02 |

NSC: 675344

| Panel/Cell Line | Log₁₀ GI50 | Log₁₀ TGI | Log₁₀ LC50 |
|---|---|---|---|
| Leukemia | | | |
| CCRF-CEM | >−4.00 | >−4.00 | >−4.00 |
| HL-60(TB) | >−4.00 | >−4.00 | >−4.00 |
| K-562 | −7.36 | >−4.00 | >−4.00 |
| MOLT-4 | >−4.00 | >−4.00 | >−4.00 |
| RPMI-8826 | >−4.00 | >−4.00 | >−4.00 |
| SR | >−4.00 | >−4.00 | >−4.00 |
| Non-Small Cell Lung Cancer | | | |
| A549/ATCC | −4.34 | >−4.00 | >−4.00 |
| EKVX | >−4.00 | >−4.00 | >−4.00 |
| HOP-62 | −4.46 | >−4.00 | >−4.00 |
| HOP-92 | −4.56 | −4.05 | >−4.00 |
| NCI-H226 | <−8.00 | <−8.00 | −6.65 |
| NCI-H23 | −4.69 | >−4.00 | >−4.00 |
| NCI-H322M | −4.68 | >−4.00 | >−4.00 |
| NCI-H460 | <−8.00 | >−4.00 | >−4.00 |
| NCI-H522 | >−4.00 | >−4.00 | >−4.00 |
| Colon Cancer | | | |
| HCC-2998 | −6.59 | −5.79 | −5.01 |
| HCT-116 | <−8.00 | −7.38 | −5.53 |
| HCT-15 | −7.59 | >4.00 | >−4.00 |
| HT29 | >−4.00 | >−4.00 | >−4.00 |
| KM12 | >−4.00 | >−4.00 | >−4.00 |
| SW-620 | >−4.00 | >−4.00 | >−4.00 |
| | −7.06 | >−4.00 | >−4.00 |
| CNS Cancer | | | |
| SF-268 | −4.63 | >−4.00 | >−4.00 |
| SF-295 | −4.57 | >−4.00 | >−4.00 |
| SF-539 | >−4.00 | >−4.00 | >−4.00 |
| SNB-19 | −4.53 | >−4.00 | >−4.00 |
| SNB-75 | −4.78 | −4.31 | >−4.00 |
| U251 | −7.60 | −4.58 | >−4.00 |
| Melanoma | | | |
| LOX IMVI | −4.46 | >−4.00 | >−4.00 |
| MALME-3M | >−4.00 | >−4.00 | >−4.00 |
| M14 | >−4.00 | >−4.00 | >−4.00 |
| SK-MEL-2 | >−4.00 | >−4.00 | >−4.00 |

-continued

NSC: 675344

| Panel/Cell Line | Log₁₀ GI50 | Log₁₀ TGI | Log₁₀ LC50 |
|---|---|---|---|
| SK-MEL-28 | >−4.00 | >−4.00 | >−4.00 |
| SK-MEL-5 | >−4.00 | >−4.00 | >−4.00 |
| UACC-257 | <−8.00 | −7.73 | −7.28 |
| UACC-62 | <−8.00 | −785 | >−4.00 |
| Ovarian Cancer | | | |
| IGROV1 | −7.91 | −7.37 | −4.79 |
| OVCAR-3 | <−8.00 | >−4.00 | >−4.00 |
| OVCAR-4 | −7.38 | >−4.00 | >−4.00 |
| OVCAR-5 | <−8.00 | −7.06 | >−4.00 |
| OVCAR-8 | >−4.00 | >−4.00 | >−4.00 |
| SK-OV-3 | −4.78 | >−4.00 | >−4.00 |
| Renal Cancer | | | |
| 786-0 | −4.91 | −4.17 | >−4.00 |
| A498 | <−8.00 | −7.74 | −7.18 |
| ACHN | −4.89 | −4.08 | >−4.00 |
| RXF-393 | −4.80 | −4.28 | >−4.00 |
| SN12C | >−4.00 | >−4.00 | >−4.00 |
| TK-10 | <−8.00 | −7.30 | >−4.00 |
| UO-31 | >−4.00 | >−4.00 | >−4.00 |
| Prostate Cancer | | | |
| PC-3 | >−4.00 | >−4.00 | >−4.00 |
| DU-145 | −4.44 | >−4.00 | >−4.00 |
| Breast Cancer | | | |
| MCF7 | −6.90 | >−4.00 | >−4.00 |
| MCF7/ADR-RES | >−4.00 | >−4.00 | >−4.00 |
| MDA-MB-231/ATCC | −4.72 | >−4.00 | >−4.00 |
| MS 578T | −4.27 | >−4.00 | >−4.00 |
| MDA-MB-435 | >−4.00 | >−4.00 | >−4.00 |
| MDA-N | >−4.00 | >−4.00 | >−4.00 |
| BT-549 | −4.37 | >−4.00 | >−4.00 |
| T-47D | −6.21 | >−4.00 | >−4.00 |
| MG_MID | −5.28 | −4.54 | −4.21 |
| Delta | 2.72 | 3.46 | 3.07 |
| Range | 4.00 | 4.00 | 3.28 |

NSC: 676630

| Panel/Cell Line | Log₁₀ GI50 | Log₁₀ TGI | Log₁₀ LC50 |
|---|---|---|---|
| Leukemia | | | |
| CCRF-CEM | >−4.00 | >−4.00 | >−4.00 |
| HL-60(TB) | >−4.00 | >−4.00 | >−4.00 |
| K-562 | −5.47 | >−4.00 | >−4.00 |
| MOLT-4 | >−4.00 | >−4.00 | >−4.00 |
| RPMI-8226 | >−4.00 | >−4.00 | >−4.00 |
| SR | >−4.00 | >−4.00 | >−4.00 |
| Non-Small Cell Lung Cancer | | | |
| A549/ATCC | −4.06 | >−4.00 | >−4.00 |
| EKVX | >−4.00 | >−4.00 | >−4.00 |
| HOP-62 | | >−4.00 | >−4.00 |
| HOP-92 | >4.00 | >−4.00 | >−4.00 |
| NCI-H226 | −6.72 | −6.31 | −5.61 |
| NCI-H23 | | >−4.00 | >−4.00 |
| NCI-H322M | >−4.00 | >−4.00 | >−4.00 |

-continued

NSC: 676630

OHC—[Se]—[S]—[Se]—CHO

| Panel/Cell Line | Log₁₀ GI50 | Log₁₀ TGI | Log₁₀ LC50 |
|---|---|---|---|
| NCI-H460 | −6.89 | >−4.00 | >−4.00 |
| NCI-H522 | −4.68 | −4.27 | >−4.00 |
| Colon Cancer | | | |
| COLO 205 | −4.03 | >−4.00 | >−4.00 |
| HCC-2998 | | −4.07 | >−4.00 |
| HCT-116 | −5.52 | >−4.00 | >−4.00 |
| HCT-15 | >−4.00 | >−4.00 | >−4.00 |
| HT29 | >−4.00 | >−4.00 | >−4.00 |
| KM12 | >−4.00 | >−4.00 | >−4.00 |
| SW-620 | >−4.00 | >−4.00 | >−4.00 |
| CNS Cancer | | | |
| SF-268 | >−4.00 | >−4.00 | >−4.00 |
| SF-295 | >−4.00 | >−4.00 | >−4.00 |
| SF-539 | >−4.00 | >−4.00 | >−4.00 |
| SNB-19 | >−4.00 | >−4.00 | >−4.00 |
| SNB-75 | −4.17 | >−4.00 | >−4.00 |
| U251 | −6.23 | >−4.00 | >−4.00 |
| Melanoma | | | |
| LOC IMVI | >−4.00 | >−4.00 | >−4.00 |
| MALME-3M | >−4.00 | >−4.00 | >−4.00 |
| M14 | >−4.00 | >−4.00 | >−4.00 |
| SK-MEL-2 | >−4.00 | >−4.00 | >−4.00 |
| SK-MEL-28 | >−4.00 | >−4.00 | >−4.00 |
| SK-MEL-5 | >−4.00 | >−4.00 | >−4.00 |
| UACC-257 | −6.56 | −6.17 | −5.16 |
| UACC-62 | −6.58 | >−4.00 | >−4.00 |
| Ovarian Cancer | | | |
| IGROV1 | −5.83 | >−4.00 | >−4.00 |
| OVCAR-3 | −6.14 | >−4.00 | >−4.00 |
| OVCAR-4 | | | >−4.00 |
| OVCAR-5 | −6.88 | −6.35 | −5.45 |
| OVCAR-8 | −4.48 | >−4.00 | >−4.00 |
| SK-OV-3 | >−4.00 | >−4.00 | >−4.00 |
| Renal Cancer | | | |
| 786-0 | >−4.00 | >−4.00 | >−4.00 |
| ACHN | >−4.00 | >−4.00 | >−4.00 |
| CAKI-1 | −6.13 | −4.81 | >−4.00 |
| RXF-393 | >−4.00 | >−4.00 | >−4.00 |
| SN12C | >−4.00 | >−4.00 | >−4.00 |
| TK-10 | −6.42 | −5.79 | >−4.00 |
| UO-31 | >−4.00 | >−4.00 | >−4.00 |
| Prostate Cancer | | | |
| PC-3 | >−4.00 | >−4.00 | >−4.00 |
| DU-145 | >−4.00 | >−4.00 | >−4.00 |
| Breast Cancer | | | |
| MCF7 | −6.17 | >−4.00 | >−4.00 |
| MCF7/ACR-RES | −4.10 | >−4.00 | >−4.00 |
| MDA-MB-231/ATCC | >−4.00 | >−4.00 | >−4.00 |
| HS 578T | >−4.00 | >−4.00 | >−4.00 |
| MDA-MB-435 | >−4.00 | >−4.00 | >−4.00 |
| MDA-N | >−4.00 | >−4.00 | >−4.00 |
| BT-549 | −4.20 | >−4.00 | >−4.00 |
| T-47D | | >−4.00 | >−4.00 |
| MG_MID | | | |
| Delta | −4.58 | −4.17 | −4.07 |
| Range | 2.31 | 2.18 | 1.54 |
| | 2.89 | 2.35 | 1.61 |

NSC: 675245

OHC—[Se]—[Se]—[Se]—CHO

| Panel/Cell Line | Log₁₀ GI50 | Log₁₀ TGI | Log₁₀ LC50 |
|---|---|---|---|
| Leukemia | | | |
| CCRF-CEM | >−4.00 | >−4.00 | >−4.00 |
| HL-60(TB) | >−4.00 | >−4.00 | >−4.00 |
| K-562 | −5.17 | >−4.00 | >−4.00 |
| MOLT-4 | >−4.00 | >−4.00 | >−4.00 |
| RPMI-8226 | >−4.00 | >−4.00 | >−4.00 |
| SR | >−4.00 | >−4.00 | >−4.00 |
| Non-Small Cell Lung Cancer | | | |
| A549/ATCC | >−4.00 | >−4.00 | >−4.00 |
| EKVX | >−4.00 | >−4.00 | >−4.00 |
| HOP-62 | −4.29 | >−4.00 | >−4.00 |
| HOP-92 | >−4.00 | >−4.00 | >−4.00 |
| NCI-H226 | −6.01 | −5.44 | >−4.00 |
| NCI-H23 | >−4.00 | >−4.00 | >−4.00 |
| NCI-H322M | >−4.00 | >−4.00 | >−4.00 |
| NCI-H460 | −5.75 | >−4.00 | >−4.00 |
| NCI-H522 | −4.66 | −4.34 | −4.02 |
| Colon Cancer | | | |
| COLO 205 | >−4.00 | >−4.00 | >−4.00 |
| HCC-2998 | −5.32 | >−4.00 | >−4.00 |
| HCT-116 | −6.16 | >−4.00 | >−4.00 |
| HCT-15 | >−4.00 | >−4.00 | >−4.00 |
| HT29 | >−4.00 | >−4.00 | >−4.00 |
| KM12 | >−4.00 | >−4.00 | >−4.00 |
| SW-620 | −5.38 | >−4.00 | >−4.00 |
| CNS Cancer | | | |
| SF-268 | >−4.00 | >−4.00 | >−4.00 |
| SF-295 | −4.31 | >−4.00 | >−4.00 |
| SF-539 | >−4.00 | >−4.00 | >−4.00 |
| SNB-19 | −4.53 | >−4.00 | >−4.00 |
| SNB-75 | −5.00 | >−4.00 | >−4.00 |
| U251 | −5.98 | >−4.00 | >−4.00 |
| Melanoma | | | |
| LOX IMVI | >−4.00 | >−4.00 | >−4.00 |
| MALME-3M | >−4.00 | >−4.00 | >−4.00 |
| M14 | >−4.00 | >−4.00 | >−4.00 |
| SK-MEL-2 | >−4.00 | >−4.00 | >−4.00 |
| SK-MEL-28 | >−4.00 | >−4.00 | >−4.00 |
| SK-MEL-5 | −4.14 | >−4.00 | >−4.00 |
| UACC-257 | −6.49 | −6.04 | >−4.00 |
| UACC-62 | −7.19 | >−4.00 | >−4.00 |
| Ovarian Cancer | | | |
| IGROV1 | −4.17 | −4.59 | −4.13 |
| OVCAR-3 | −6.41 | >−4.00 | >−4.00 |
| OVCAR-4 | −5.58 | >−4.00 | >−4.00 |
| OVCAR-5 | −6.11 | >−4.00 | >−4.00 |
| OVCAR-8 | >−4.00 | >−4.00 | >−4.00 |
| Renal Cancer | | | |
| 786-0 | −4.17 | >−4.00 | >−4.00 |
| A498 | −6.51 | −6.05 | −5.17 |
| ACHN | −4.24 | >−4.00 | >−4.00 |
| CAKI-1 | −6.57 | −6.03 | >−4.00 |
| RXF-393 | −4.92 | >−4.00 | >−4.00 |
| SN12C | >−4.00 | >−4.00 | >−4.00 |
| TK-10 | −6.59 | −6.09 | >−4.00 |
| UO-31 | >−4.00 | >−4.00 | >−4.00 |
| Prostate Cancer | | | |
| PC-3 | >−4.00 | >−4.00 | >−4.00 |
| DU-145 | >−4.00 | >−4.00 | >−4.00 |

-continued

NSC: 675245

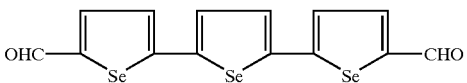

| Panel/Cell Line | Log₁₀ GI50 | Log₁₀ TGI | Log₁₀ LC50 |
|---|---|---|---|
| Breast Cancer | | | |
| MCF7 | −5.83 | >−4.00 | >−4.00 |
| MCF7/ADR-RES | >−4.00 | >−4.00 | >−4.00 |
| MDA-MB-231/ATCC | >−4.00 | >−4.00 | >−4.00 |
| HS 578T | −4.06 | >−4.00 | >−4.00 |
| MDA-MB-435 | >−4.00 | >−4.00 | >−4.00 |
| MDA-N | >−4.00 | >−4.00 | >−4.00 |
| BT-549 | >−4.00 | >−4.00 | >−4.00 |
| T-47D | −4.80 | >−4.00 | >−4.00 |
| MG_MID | | | |
| Delta | −4.67 | −4.18 | −4.02 |
| Range | 2.53 | 1.91 | 1.15 |
| | 3.19 | 2.09 | 1.17 |

NSC: 675244

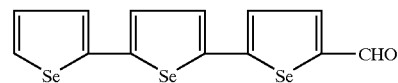

| Panel/Cell Line | Log₁₀ GI50 | Log₁₀ TGI | Log₁₀ LC50 |
|---|---|---|---|
| Leukemia | | | |
| CCRF-CEM | −5.67 | −5.15 | >−4.00 |
| HL-60(TB) | −5.61 | | >−4.00 |
| K-562 | −5.87 | −4.48 | >−4.00 |
| MOLT-4 | −5.62 | −5.12 | >−4.00 |
| RPMI-8226 | −5.53 | >−4.00 | >−4.00 |
| | −5.39 | | |
| Non-Small Cell Lung Cancer | | | |
| A549/ATCC | −4.87 | −4.58 | −4.29 |
| EKVX | −4.60 | −4.19 | >−4.00 |
| HOP-62 | −4.92 | −4.53 | −4.13 |
| HOP-92 | −4.96 | −4.59 | −4.20 |
| NCI-H226 | −5.65 | −5.29 | −4.41 |
| NCI-H23 | −4.87 | −4.51 | −4.16 |
| NCI-H322M | −4.88 | −4.55 | −4.22 |
| NCI-H460 | −5.65 | −4.79 | −4.39 |
| NCI-H522 | −5.28 | −4.76 | −4.37 |
| Colon Cancer | | | |
| COLO 205 | −5.50 | −4.92 | −4.46 |
| HCC-2998 | −5.60 | −4.94 | −4.41 |
| HCT-116 | −6.42 | −4.86 | −4.41 |
| HCT-15 | −5.13 | −4.58 | −4.10 |
| HT29 | −5.49 | −4.88 | −4.44 |
| KM12 | −5.20 | −4.71 | −4.34 |
| SW-620 | | | |
| CNS Cancer | | | |
| SF-268 | −5.35 | −4.24 | >−4.00 |
| SF-295 | −4.82 | −4.55 | −4.27 |
| SF-539 | −4.77 | −4.48 | −4.20 |
| SNB-19 | −4.99 | −4.52 | −4.06 |
| SNB-75 | −5.70 | −5.19 | >−4.00 |
| U251 | −6.50 | −4.86 | −4.32 |
| Melanoma | | | |
| LOX IMVI | −5.25 | −4.68 | −4.11 |
| MALME-3M | −4.90 | −4.55 | −4.19 |

-continued

NSC: 675244

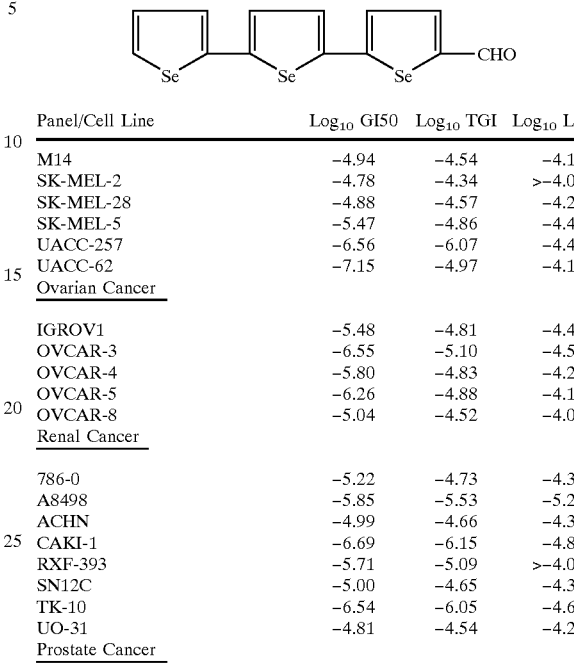

| Panel/Cell Line | Log₁₀ GI50 | Log₁₀ TGI | Log₁₀ LC50 |
|---|---|---|---|
| M14 | −4.94 | −4.54 | −4.14 |
| SK-MEL-2 | −4.78 | −4.34 | >−4.00 |
| SK-MEL-28 | −4.88 | −4.57 | −4.26 |
| SK-MEL-5 | −5.47 | −4.86 | −4.43 |
| UACC-257 | −6.56 | −6.07 | −4.48 |
| UACC-62 | −7.15 | −4.97 | −4.18 |
| Ovarian Cancer | | | |
| IGROV1 | −5.48 | −4.81 | −4.40 |
| OVCAR-3 | −6.55 | −5.10 | −4.51 |
| OVCAR-4 | −5.80 | −4.83 | −4.22 |
| OVCAR-5 | −6.26 | −4.88 | −4.12 |
| OVCAR-8 | −5.04 | −4.52 | −4.02 |
| Renal Cancer | | | |
| 786-0 | −5.22 | −4.73 | −4.36 |
| A8498 | −5.85 | −5.53 | −5.20 |
| ACHN | −4.99 | −4.66 | −4.33 |
| CAKI-1 | −6.69 | −6.15 | −4.84 |
| RXF-393 | −5.71 | −5.09 | >−4.00 |
| SN12C | −5.00 | −4.65 | −4.30 |
| TK-10 | −6.54 | −6.05 | −4.60 |
| UO-31 | −4.81 | −4.54 | −4.27 |
| Prostate Cancer | | | |
| PC-3 | −4.92 | −4.49 | −4.06 |
| DU-145 | −4.90 | −4.60 | −4.29 |
| Breast Cancer | | | |
| MCF7 | −6.32 | −4.94 | −4.36 |
| MCF7/ADR-RES | | | |
| HS 578T | −5.14 | −4.66 | −4.27 |
| MDA-MB-435 | −4.99 | −4.48 | >−4.00 |
| MDA-N | −5.34 | −4.71 | −4.19 |
| BT-549 | −4.91 | −4.51 | −4.10 |
| T-47D | −4.95 | −4.63 | −4.32 |
| | −5.42 | −4.45 | >−4.00 |
| MG_MID | | | |
| Delta | −5.43 | −4.78 | −4.25 |
| Range | 1.72 | 1.37 | 0.96 |
| | 2.55 | 2.15 | 1.20 |

NSC: 675346

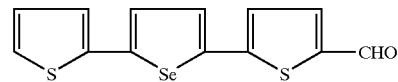

| Panel/Cell Line | Log₁₀ GI50 | Log₁₀ TGI | Log₁₀ LC50 |
|---|---|---|---|
| Leukemia | | | |
| CCRF-CEM | >−4.00 | >−4.00 | >−4.00 |
| HL-60(TB) | >−4.00 | >−4.00 | >−4.00 |
| K-562 | −5.64 | >−4.00 | >−4.00 |
| MOLT-4 | >−4.00 | >−4.00 | >−4.00 |
| RPMI-8226 | >−4.00 | >−4.00 | >−4.00 |
| SR | >−4.00 | >−4.00 | >−4.00 |
| Non-Small Cell Lung Cancer | | | |
| A549/ATCC | −4.26 | >−4.00 | >−4.00 |
| EKVX | −4.11 | >−4.00 | >−4.00 |
| HOP-62 | −4.19 | >−4.00 | >−4.00 |

-continued

NSC: 675346

| Panel/Cell Line | Log₁₀ GI50 | Log₁₀ TGI | Log₁₀ LC50 |
|---|---|---|---|
| HOP-92 | −4.73 | −4.15 | >−4.00 |
| NCI-H226 | −7.76 | −6.92 | −5.98 |
| NCI-H23 | −4.84 | −4.23 | >−4.00 |
| NCI-H322M | −4.89 | >−4.00 | >−4.00 |
| NCI-H460 | −6.60 | >−4.00 | >−4.00 |
| NCI-H522 | −4.48 | >−4.00 | >−4.00 |
| Colon Cancer | | | |
| COLO 205 | −5.32 | >−4.00 | >−4.00 |
| HCC-2998 | −6.63 | 6.15 | −4.68 |
| HCT-116 | −6.94 | >−4.00 | >−4.00 |
| HCT-15 | −4.73 | >−4.00 | >−4.00 |
| HT29 | >−4.00 | >−4.00 | >−4.00 |
| KM12 | −4.49 | >−4.00 | >−4.00 |
| SW-620 | | >−4.00 | >−4.00 |
| | | >−4.00 | >−4.00 |
| CNS Cancer | | | |
| SF-268 | −4.72 | >−4.00 | >−4.00 |
| SF-295 | −4.67 | −4.16 | >−4.00 |
| SF-539 | −4.29 | >−4.00 | >−4.00 |
| SNB-19 | −4.66 | −4.02 | >−4.00 |
| SNB-75 | −4.86 | −4.24 | >−4.00 |
| U251 | −7.24 | −4.59 | >−4.00 |
| Melanoma | | | |
| LOX IMVI | −4.71 | >−4.00 | >−4.00 |
| MALME-3M | −4.46 | >−4.00 | >−4.00 |
| M14 | −4.55 | >−4.00 | >−4.00 |
| SK-MEL-2 | −4.61 | >−4.00 | >−4.00 |
| SK-MEL-28 | −4.35 | >−4.00 | >−4.00 |
| SK-MEL-5 | −4.33 | >−4.00 | >−4.00 |
| UACC-257 | −7.58 | −7.08 | −6.51 |
| UACC-62 | <−8.00 | −7.55 | −4.07 |
| Ovarian Cancer | | | |
| IGROV1 | −6.79 | −6.25 | >−4.00 |
| OVCAR-3 | −7.72 | −4.67 | >−4.00 |
| OVCAR-4 | −6.92 | −4.57 | >−4.00 |
| OVCAR-5 | −7.35 | −6.24 | >−4.00 |
| OVCAR-8 | −5.35 | >−4.00 | >−4.00 |
| SK-OV-3 | −4.90 | >−4.00 | >−4.00 |
| Renal Cancer | | | |
| 786-0 | −4.87 | >−4.00 | >−4.00 |
| A498 | −6.84 | −6.53 | −6.03 |
| ACHN | −4.64 | >−4.00 | >−4.00 |
| RXF-393 | −4.79 | −4.37 | >−4.00 |
| SN12C | >−4.00 | >−4.00 | >−4.00 |
| TK-10 | −7.20 | −6.38 | −4.27 |
| UO-31 | −4.45 | >−4.00 | >−4.00 |
| Prostate Cancer | | | |
| PC-3 | −4.21 | >−4.00 | >−4.00 |
| DU-145 | −4.54 | >−4.00 | >−4.00 |
| Breast Cancer | | | |
| MCF7 | −6.09 | >−4.00 | >−4.00 |
| MCF7/ADR-RES | −4.88 | −4.22 | >−4.00 |
| HS 578T | −4.63 | >−4.00 | >−4.00 |
| MDA-MB-435 | −4.55 | −4.06 | >−4.00 |
| MDA-N | >−4.00 | >−4.00 | >−4.00 |
| BT-549 | −4.00 | >−4.00 | >−4.00 |
| T-47D | −4.74 | −4.39 | −4.04 |
| | −5.77 | >−4.00 | >−4.00 |

-continued

NSC: 675346

| Panel/Cell Line | Log₁₀ GI50 | Log₁₀ TGI | Log₁₀ LC50 |
|---|---|---|---|
| MG_MID | | | |
| Delta | −5.17 | −4.42 | −4.13 |
| Range | 2.83 | 3.13 | 2.38 |
| | 4.00 | 3.55 | 2.51 |

NSC: 675345

| Panel/Cell Line | Log₁₀ GI50 | Log₁₀ TGI | Log₁₀ LC50 |
|---|---|---|---|
| Leukemia | | | |
| CCRF-CEM | >−4.00 | >−4.00 | >−4.00 |
| HL-60(TB) | >−4.00 | >−4.00 | >−4.00 |
| K-562 | −4.51 | >−4.00 | >−4.00 |
| MOLT-4 | >−4.00 | >−4.00 | >−4.00 |
| RPMI-8226 | >−4.00 | >−4.00 | >−4.00 |
| SR | >−4.00 | >−4.00 | >−4.00 |
| Non-Small Cell Lung Cancer | | | |
| A549/ATCC | >−4.00 | >−4.00 | >−4.00 |
| EKVX | >−4.00 | >−4.00 | >−4.00 |
| HOP-62 | −4.32 | >−4.00 | >−4.00 |
| HOP-92 | −4.84 | −4.26 | >−4.00 |
| NCI-H226 | −6.24 | −5.62 | −5.07 |
| NCI-H23 | −4.66 | >−4.00 | >−4.00 |
| NCI-H322M | >−4.00 | >−4.00 | >−4.00 |
| NCI-H460 | −6.09 | >−4.00 | >−4.00 |
| NCI-H522 | −4.07 | >−4.00 | >−4.00 |
| Colon Cancer | | | |
| COLO 205 | −4.47 | >−4.00 | >−4.00 |
| HCC-2998 | −5.63 | −5.16 | −4.13 |
| HCT-116 | −5.39 | >−4.00 | >−4.00 |
| HCT-15 | >−4.00 | >−4.00 | >−4.00 |
| HT29 | >−4.00 | >−4.00 | >−4.00 |
| KM12 | >−4.00 | >−4.00 | >−4.00 |
| SW-620 | −4.42 | >−4.00 | >−4.00 |
| CNS Cancer | | | |
| SF-268 | >−4.00 | >−4.00 | >−4.00 |
| SF-295 | −4.41 | >−4.00 | >−4.00 |
| SF-539 | >−4.00 | >−4.00 | >−4.00 |
| SNB-19 | −4.50 | >−4.00 | >−4.00 |
| SNB-75 | −4.28 | >−4.00 | >−4.00 |
| U251 | −5.64 | −4.67 | −4.05 |
| Melanoma | | | |
| LOX IMVI | >−4.00 | >−4.00 | >−4.00 |
| MALME-3M | >−4.00 | >−4.00 | >−4.00 |
| M14 | >−4.00 | >−4.00 | >−4.00 |
| SK-MEL-2 | −4.11 | >−4.00 | >−4.00 |
| SK-MEL-28 | >−4.00 | >−4 00 | >−4.00 |
| SK-MEL-5 | >−4.00 | >−4.00 | >−4.00 |
| UACC-257 | −5.86 | >−4.00 | −5.24 |
| UACC-62 | −6.46 | −5.55 | >−4.00 |
| Ovarian Cancer | | | |
| IGROV1 | −5.36 | −4.64 | >−4.00 |
| OVCAR-3 | −5.66 | >−4.00 | −5.39 |

-continued

NSC: 675345

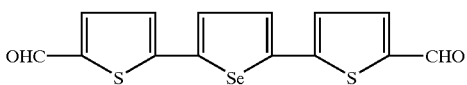

| Panel/Cell Line | Log₁₀ GI50 | Log₁₀ TGI | Log₁₀ LC50 |
|---|---|---|---|
| OVCAR-4 |  | >−4.00 | >−4.00 |
| OVCAR-5 | −5.81 | −5.27 | >−4.00 |
| OVCAR-8 | >−4.00 | >−4.00 | >−4.00 |
| SK-OV-3 | −4.26 | >−4.00 | >−4.00 |
| Renal Cancer | | | |
| 786-0 | −4.96 | >−4.00 | >−4.00 |
| A498 | −6.32 | −5.81 | −5.39 |
| ACHN | −4.11 | >−4.00 | >−4.00 |
| CAKI-1 | −4.49 | >−4.00 | >−4.00 |
| RXF-393 | >−4.00 | >−4.00 | >−4.00 |
| SN12C | −6.59 | −5.78 | >−4.00 |
| TK-10 | >−4.00 | >−4.00 | >−4.00 |
| UO-31 | | | |
| Prostate Cancer | | | |
| PC-3 | >−4.00 | >−4.00 | >−4.00 |
| DU-145 | >−4.00 | >−4.00 | >−4.00 |
| Breast Cancer | | | |
| MCF7 | −6.14 | −5.25 | >−4.00 |
| MCF7/ADR-RES | >−4.00 | >−4.00 | >−4.00 |
| MDA-MB-231/ATC | −4.74 | >−4.00 | >−4.00 |
| HS 578T | −4.17 | >−4.00 | >−4.00 |
| MDA-MB-435 | −4.23 | >−4.00 | >−4.00 |
| MDA-N | >−4.00 | >−4.00 | >−4.00 |
| BT-549 | >−4.00 | >−4.00 | >−4.00 |
| T-47D | −4.10 | >−4.00 | >−4.00 |
| MG_MID | | | |
| Delta | −4.75 | −4.21 | −4.07 |
| Range | 2.03 | 1.61 | 1.32 |
|  | 2.59 | 1.81 | 1.39 |

EXAMPLE 54
Inhibition of Protein Kinase C

The Protein Kinase C (PKC) screening assay utilized in the following experiments is similar to standard PKC assays used by many investigators. Its primary features are that 1) the assay utilizes a 50:50 mixture of recombinant mouse PKCα and mouse PKCβ₂; 2) employs histone as phosphate-accepting substrate; and 3) the PKC enzymatic activity is activated with phosphatidylserine, TPA and low concentration of calcium, so that both calcium and TPA are somewhat limiting for the extent of activation. In this manner the assay is sensitive to inhibitors of PKC activation. A more detailed description of the assay is provided in the following paragraphs.

The recombinant PKC formulation is a mixture (equal parts by activity) of mouse PKCα and mouse PKCβ₂. The enzymes are expressed in Sf9 insect cells from recombinant baculovirus and partially purified on DEAE-cellulose and Sephacryl 200 gel filtration. Sufficient PKC is added to each reaction to provide approximately 4 pmols phosphate transferred in 30 minute (per total reaction.) The reaction is linear over the time when 4 pmols of phosphate is transferred and the reaction remains linear well beyond this time frame.

The PKC screening assay is performed in 96 well polystyrene U bottom micro titer plates, in a total reaction volume of 50 ul. Solution manipulations are performed during the assay utilize a Rainin, motorized EDP-plus M8 eight-channel micropipettor.

Samples were typically assayed at three dilutions, however some highly active pure compounds were assayed at six dilutions. Assay samples are dissolved in DMSO at a concentration of 10 mg/ml or less for samples suspected of being more potent. In some cases 50% DMSO:water, water, or methanol is substituted (if essential) for the solvent. At least 25 µl of the highest concentration sample to be assayed is transferred to a well in a 96 well U-bottom polystyrene assay plate. Serial 5-fold or 10-fold dilutions (depending on the dose-range desired) are made using the EDP-plus M8 eight-channel pipettor in dilute mode and mixing by repipetting. Using the 8-channel pipettor, 2 µl of each dilution is transferred to the appropriate wells of the plate(s) to be used for each assay. Duplicate assays are performed for each dose, with each assay, allowing six wells (half the row) for three-dose assays, or 12 wells (the whole row) for six-dose assays. In general, extracts and fractions are assayed at three doses: 400, 40 an 4 ug/ml, while pure compounds are tested at six doses: 400, 80, 16, 3.2, 0.64, 0.128 (8-fold series). The results of these experiments are shown in Table 2.

TABLE 2

Inhibition of Protein Kinase C

| Compounds, NSC# | Structure | IC₅₀ (µg/ml) |
|---|---|---|
| 675347 | (structure) | $1 \times 10^0$ |
| 675346 | (structure) | $5 \times 10^{-1}$ |
| 675345 | (structure) | $9 \times 10^{-1}$ |
| 675344 | (structure) | $5 \times 10^1$ |

TABLE 2-continued

Inhibition of Protein Kinase C

| Compounds, NSC# | Structure | IC$_{50}$ ($\mu$g/ml) |
| --- | --- | --- |
| 675343 | HOH$_2$C—[S]—[Se]—[S]—CH$_2$OH | $3 \times 10^1$ |
| 676628 | [Se]—[S]—[Se] | $1 \times 10^0$ |
| 676629 | [Se]—[S]—[Se]—CHO | $2 \times 10^{-1}$ |
| 676630 | OHC—[Se]—[S]—[Se]—CHO | $9 \times 10^{-1}$ |
| 676631 | [Se]—[S]—[Se]—CH$_2$OH | $2 \times 10^0$ |
| 676632 | HOH$_2$C—[Se]—[S]—[Se]—CH$_2$OH | $5 \times 10^1$ |
| 676633 | [Se]—[NH]—[Se] | $6 \times 10^0$ |
| 676634 | [Se]—[NH]—[Se]—CHO | $8 \times 10^{-1}$ |
| 676635 | [Se]—[NH]—[Se]—CH$_2$OH | $8 \times 10^0$ |
| 674973 | [Se]—[Se]—[Se] | $7 \times 10^0$ |
| 675244 | [Se]—[Se]—[Se]—CHO | $1 \times 10^0$ |
| 675245 | OHC—[Se]—[Se]—[Se]—CHO | $1 \times 10^0$ |
| 675246 | [Se]—[Se]—[Se]—CH$_2$OH | $3 \times 10^0$ |
| 675247 | HOH$_2$C—[Se]—[Se]—[Se]—CH$_2$OH | $1 \times 10^1$ |

What is claimed is:

1. A compound of formula I:

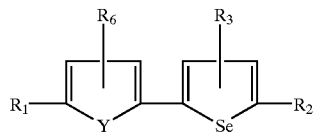

wherein $R_1$ and $R_2$ are independently selected from the group consisting of

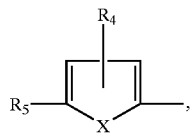

H, $CH_2OH$, CHO and $CH_2NH_2$;

X and Y are independently selected from the group consisting of Se, S, O, and NR, wherein R is H or $C_1$–$C_7$ alkyl;

$R_3$, $R_4$, $R_5$ and $R_6$ are independently selected from the group consisting of H, CHO, $CH_2OH$ and $CH_2NH_2$;

and when $R_1$, $R_2$, $R_3$, $R_4$, $R_5$ or $R_6$ is $CH_2NH_2$, the pharmaceutically acceptable salt of the compound represented thereby; with the provisos, that $R_1$ and $R_2$ are not both

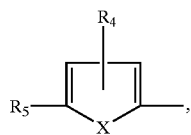

and that one of $R_1$ or $R_2$ is

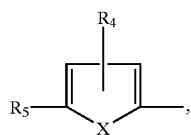

and when $R_2$ is

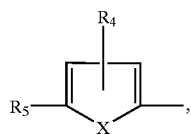

one of $R_1$, $R_3$, $R_4$, $R_5$ and $R_6$ is other than H; and when $R_1$ is

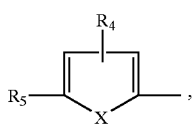

one of $R_2$, $R_3$, $R_4$, $R_5$ and $R_6$ is other than H.

2. The compound of claim 1, wherein $R_3$, $R_4$ and $R_6$ are H.

3. The compound of claim 2 wherein $R_2$ is selected from the group consisting of H, $CH_2OH$, CHO and $CH_2NH_2$ and $R_1$ is

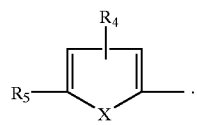

4. The compound of claim 2 wherein $R_1$ is selected from the group consisting of H, $CH_2OH$, CHO and $CH_2NH_2$ and $R_2$ is

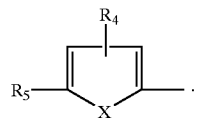

5. The compound of claim 3 wherein X is Se.

6. A compound of formula I:

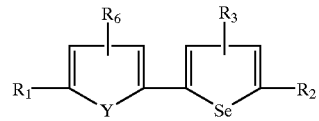

wherein $R_1$ and $R_2$ are independently selected from the group consisting of

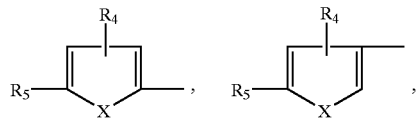

H, CHO, $CH_2OH$ and $CH_2NH_2$;

X and Y are independently selected from the group consisting of Se, S, O and NR, wherein R is H or $C_1$–$C_7$ alkyl; $R_3$, $R_4$, $R_5$ and $R_6$ are independently selected from the group consisting of H, CHO, $CH_2OH$ and $CH_2NH_2$;

and when $R_1$, $R_2$, $R_3$, $R_4$, $R_5$ or $R_6$ is $CH_2NH_2$, the pharmaceutically acceptable salt of the compound represented thereby; with the proviso that $R_1$ and $R_2$ are not both hydrogen and with the proviso that one of $R_1$ or $R_2$ is

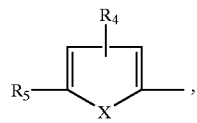

and when $R_2$ is

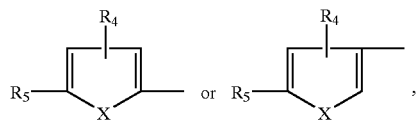

$R_1$ is H, CHO, $CH_2OH$ or $CH_2NH_2$, provided that at least one of $R_1$ $R_3$, $R_4$, $R_5$ and $R_6$ is other than H;

and when $R_1$ is

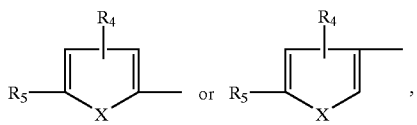

$R_2$ is H, CHO, CH$_2$OH or CH$_2$NH$_2$, provided that at least one of $R_2$, $R_3$, $R_4$, $R_5$ and $R_6$ is other than H.

7. A pharmaceutical composition comprising a compound of formula I:

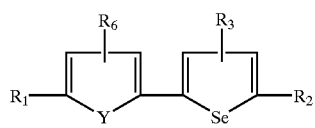

wherein $R_1$ and $R_2$ are independently selected from the group consisting of;

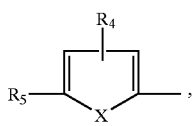

H, CH$_2$OH, CHO and CH$_2$NH$_2$;

X and Y are independently selected from the group consisting of Se, S, O and NR, wherein R is H or C$_1$–C$_7$ alkyl;

$R_3$, $R_4$, $R_5$ and $R_6$ are independently selected from the group consisting of H, CHO, CH$_2$OH and CH$_2$NH$_2$; and when $R_1$, $R_2$, $R_3$, $R_4$, $R_5$ or $R_6$ is CH$_2$NH$_2$, the pharmaceutically acceptable salt of the compound represented thereby; with the proviso that $R_1$ and $R_2$ are not both

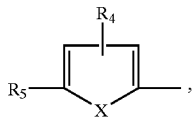

and with the proviso that one of $R_1$ or $R_2$ is

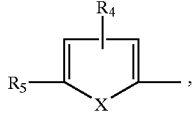

and at least one of $R_1$, $R_2$, $R_3$, $R_4$, $R_5$ or $R_6$ is other than hydrogen and a pharmaceutically acceptable carrier.

8. The composition of claim 7, wherein $R_3$, $R_4$ and $R_6$ in the compound are H.

9. The composition of claim 8 wherein $R_2$ in the compound is selected from the group consisting of H, CH$_2$OH, CHO and CH$_2$NH$_2$ and $R_1$ is

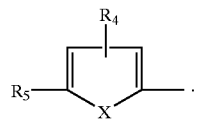

10. The composition of claim 8 wherein $R_1$ in the compound is selected from the group consisting of H, CH$_2$OH, CHO and CH$_2$NH$_2$ and $R_2$ is

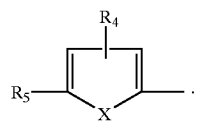

11. The composition of claim 9 wherein X in the compound is Se.

12. The compound of claim 4 wherein X is Se.

13. The composition of claim 10 wherein X in the compound is Se.

14. The compound of claim 1 complexed with a cyclodextrin.

15. The compound of claim 6 complexed with a cyclodextrin.

16. The pharmaceutical composition of claim 7 wherein the compound is complexed with a cyclodextrin.

17. A compound of formula I:

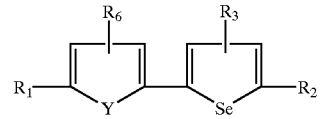

wherein $R_1$ and $R_2$ are independently selected form the group consisting of

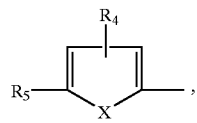

H, CH$_2$OH, CHO and CH$_2$NH$_2$;

X is Se;

Y is NR, wherein R is H or C$_1$–C$_7$ alkyl;

$R_3$, $R_4$, $R_5$ and $R_6$ are independently selected from the group consisting of H, CHO, CH$_2$OH and CH$_2$NH$_2$;

and when $R_1$, $R_2$, $R_3$, $R_4$, $R_5$ or $R_6$ is CH$_2$NH$_2$, the pharmaceutically acceptable salt of the compound represented thereby; with the provisos, that $R_1$ and $R_2$ are not both

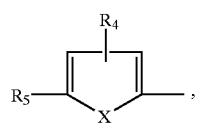

and with the proviso that one of $R_1$ or $R_2$ is

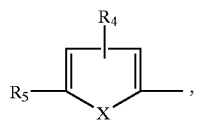

and when $R_2$ is

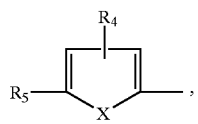

one of $R_1$, $R_3$, $R_4$, $R_5$ and $R_6$ is other than H;
and when $R_1$ is

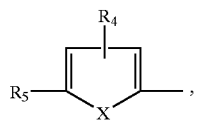

one of $R_2$, $R_3$, $R_4$, $R_5$ and $R_6$ is other than H.

18. A compound of formula I:

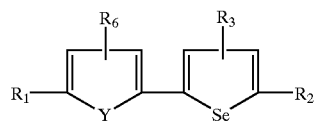

wherein $R_1$ and $R_2$ are independently selected from the group consisting of

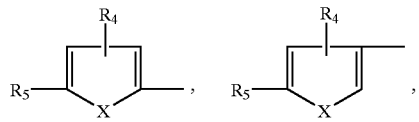

H, CHO, CH$_2$OH and CH$_2$NH$_2$ with the proviso that one of $R_1$ or $R_2$ is

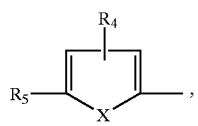

X is Se;

Y is NR, wherein R is H or C$_1$–C$_7$ alkyl; $R_3$, $R_4$, $R_5$ and $R_6$ are independently selected from the group consisting of H, CHO, CH$_2$OH and CH$_2$NH$_2$;

and when $R_1$, $R_2$, $R_3$, $R_4$, $R_5$ or $R6$ is CH$_2$NH$_2$, the pharmaceutically acceptable salt of the compound represented thereby; with the proviso that $R_1$ and $R_2$ are not both hydrogen;

and when $R_2$ is

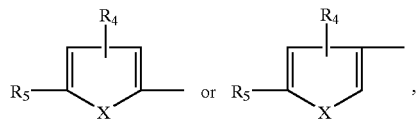

$R_1$ is H, CHO, CH$_2$OH or CH$_2$NH$_2$, provided that at least one of $R_1$ $R_3$, $R_4$, $R_5$ and $R_6$ is other than H;

and when $R_1$ is

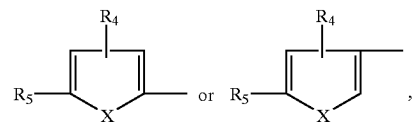

$R_2$ is H, CHO, CH$_2$OH or CH$_2$NH$_2$, provided that at least one of $R_2$, $R_3$, $R_4$, $R_5$ and $R_6$ is other than H.

19. A pharmaceutical composition comprising a compound of formula I:

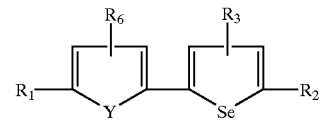

wherein $R_1$ and $R_2$ are independently selected from the group consisting of;

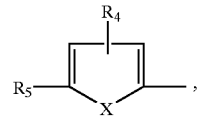

H, CH$_2$OH, CHO and CH$_2$NH$_2$;

X is Se;

Y is NR, wherein R is H or C$_1$–C$_7$ alkyl;

$R_3$, $R_4$, $R_5$ and $R_6$ are independently selected from the group consisting of H, CHO, CH$_2$OH and CH$_2$NH$_2$; and when $R_1$, $R_2$, $R_3$, $R_4$, $R_5$ or $R_6$ is CH$_2$NH$_2$, the pharmaceutically acceptable salt of the compound represented thereby; with the proviso that $R_1$ and $R_2$ are not both

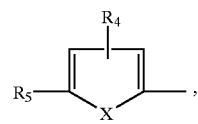

and with the proviso that one of $R_1$ or $R_2$ is

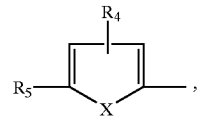

and at least one of $R_1$, $R_2$, $R_3$, $R_4$, $R_5$ or $R_6$ is other than hydrogen;

and a pharmaceutically acceptable carrier.

20. The composition of claim 19, wherein $R_3$, $R_4$ and $R_6$ in the compound are H.

21. The composition of claim 20 wherein $R_2$ in the compound is selected from the group consisting of H, $CH_2OH$, CHO and $CH_2NH_2$ and $R_1$ is

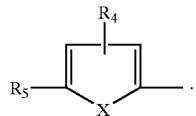

22. The composition of claim 20 wherein $R_1$ in the compound is selected from the group consisting of H, $CH_2OH$, CHO and $CH_2NH_2$ and $R_2$ is

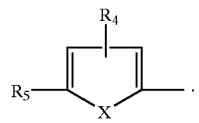

23. The compound of claim 1 wherein $R_1$ is

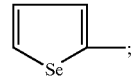

$R_2$ is $CH_2OH$;
Y is $NCH_3$; and
$R_3$, $R_4$, $R_5$ and $R_6$ are H.

* * * * *